United States Patent
Deffenbaugh et al.

(10) Patent No.: US 7,927,335 B2
(45) Date of Patent: Apr. 19, 2011

(54) INSTRUMENT FOR PREPARING AN IMPLANT SUPPORT SURFACE AND ASSOCIATED METHOD

(75) Inventors: Daren L. Deffenbaugh, Winona Lake, IN (US); Jared R. Shoup, Cordova, TN (US); Joseph P. Iannotti, Solon, OH (US)

(73) Assignee: Depuy Products, Inc., Warsaw, IN (US)

(*) Notice: Subject to any disclaimer, the term of this patent is extended or adjusted under 35 U.S.C. 154(b) by 1195 days.

(21) Appl. No.: 10/950,615

(22) Filed: Sep. 27, 2004

(65) Prior Publication Data

US 2006/0074430 A1    Apr. 6, 2006

(51) Int. Cl.
*A61B 17/58* (2006.01)
*A61F 2/00* (2006.01)

(52) U.S. Cl. .......................................... 606/87
(58) Field of Classification Search .............. 606/86–89; 623/19.11–19.14
See application file for complete search history.

(56) References Cited

U.S. PATENT DOCUMENTS

| | | |
|---|---|---|
| 3,837,008 A | 9/1974 | Bahler et al. |
| 3,855,638 A | 12/1974 | Pilliar |
| 4,040,130 A | 8/1977 | Laure |
| 4,106,128 A | 8/1978 | Greenwald et al. |
| 4,172,296 A | 10/1979 | D'Errico |
| 4,180,871 A | 1/1980 | Hamas |
| 4,550,450 A | 11/1985 | Kinnett |
| D285,968 S | 9/1986 | Kinnett |
| 4,693,723 A | 9/1987 | Gabard |
| 4,695,282 A | 9/1987 | Forte et al. |
| 4,865,025 A * | 9/1989 | Buzzi et al. ............... 606/96 |
| 4,865,605 A | 9/1989 | Dines et al. |
| 4,919,670 A | 4/1990 | Dale et al. |
| 4,964,865 A | 10/1990 | Burkhead et al. |
| 4,987,904 A | 1/1991 | Wilson |
| 5,030,219 A | 7/1991 | Matsen, III et al. |
| 5,047,058 A | 9/1991 | Roberts et al. |
| 5,108,446 A | 4/1992 | Wagner et al. |
| 5,197,465 A | 3/1993 | Montgomery |
| 5,201,882 A | 4/1993 | Paxson |
| 5,304,181 A * | 4/1994 | Caspari et al. ............. 606/80 |
| 5,314,479 A | 5/1994 | Rockwood et al. |
| 5,344,461 A | 9/1994 | Phlipot |
| 5,358,526 A | 10/1994 | Tornier |
| 5,387,241 A | 2/1995 | Hayes |
| 5,437,677 A * | 8/1995 | Shearer et al. ............. 606/96 |
| 5,458,637 A | 10/1995 | Hayes |
| 5,474,559 A | 12/1995 | Bertin et al. |
| 5,486,180 A | 1/1996 | Dietz et al. |
| 5,489,309 A | 2/1996 | Lackey et al. |
| 5,489,310 A * | 2/1996 | Mikhail ................. 623/19.11 |

(Continued)

FOREIGN PATENT DOCUMENTS

EP    01/03246 A1    3/1984

(Continued)

*Primary Examiner* — Anu Ramana

(57) ABSTRACT

An instrument for preparing a surface of a joint is provided. The glenoid surface is adapted for receiving a prosthetic component having a feature closely conforming to the surface. The prosthetic component provides a bearing surface for a head portion of a long bone. The instrument includes a guide having a first feature and a second feature and a tool. The tool is used for cooperation with the first feature for preparing the surface. The first feature is adapted to at least partially control the position of the tool as it prepares the surface. The second feature is adapted to assist in positioning of the guide with respect to the joint.

13 Claims, 30 Drawing Sheets

U.S. PATENT DOCUMENTS

| | | | |
|---|---|---|---|
| 5,496,324 A * | 3/1996 | Barnes | 606/79 |
| 5,507,821 A | 4/1996 | Sennwald et al. | |
| 5,554,158 A * | 9/1996 | Vinciguerra et al. | 606/80 |
| 5,593,441 A | 1/1997 | Lichtenstein et al. | |
| 5,593,448 A | 1/1997 | Dong | |
| 5,601,563 A | 2/1997 | Burke et al. | |
| 5,665,090 A | 9/1997 | Rockwood et al. | |
| 5,716,360 A * | 2/1998 | Baldwin et al. | 606/80 |
| 5,723,018 A | 3/1998 | Cyprien et al. | |
| 5,743,915 A | 4/1998 | Bertin et al. | |
| 5,769,855 A | 6/1998 | Bertin et al. | |
| 5,769,856 A * | 6/1998 | Dong et al. | 606/96 |
| 5,779,710 A | 7/1998 | Matsen | |
| 5,782,924 A | 7/1998 | Johnson | |
| 5,800,551 A | 9/1998 | Williamson et al. | |
| 5,853,415 A | 12/1998 | Bertin et al. | |
| 5,860,981 A | 1/1999 | Bertin et al. | |
| 5,879,401 A | 3/1999 | Besemer et al. | |
| 5,908,424 A | 6/1999 | Bertin et al. | |
| 5,928,285 A | 7/1999 | Bigliani et al. | |
| 5,976,145 A * | 11/1999 | Kennefick, III | 606/80 |
| 6,045,582 A | 4/2000 | Prybyla | |
| 6,096,084 A | 8/2000 | Townley | |
| 6,197,062 B1 | 3/2001 | Fenlin | |
| 6,197,063 B1 | 3/2001 | Dews | |
| 6,206,925 B1 | 3/2001 | Tornier | |
| 6,228,119 B1 | 5/2001 | Ondrla et al. | |
| 6,228,900 B1 | 5/2001 | Shen et al. | |
| 6,245,074 B1 | 6/2001 | Allard et al. | |
| 6,281,264 B1 | 8/2001 | Salovey et al. | |
| 6,364,910 B1 * | 4/2002 | Shultz et al. | 623/19.13 |
| 6,368,353 B1 | 4/2002 | Arcand | |
| 6,379,386 B1 * | 4/2002 | Resch et al. | 623/19.13 |
| 6,406,495 B1 | 6/2002 | Schoch | |
| 6,514,287 B2 | 2/2003 | Ondrla et al. | |
| 6,620,197 B2 | 9/2003 | Maroney et al. | |
| 6,676,705 B1 | 1/2004 | Wolf | |
| 6,679,916 B1 | 1/2004 | Frankle et al. | |
| 6,699,289 B2 | 3/2004 | Iannotti et al. | |
| 6,896,702 B2 | 5/2005 | Collazo | |
| 7,051,451 B2 | 5/2006 | Augostino et al. | |
| 7,090,677 B2 * | 8/2006 | Fallin et al. | 606/80 |
| 7,160,331 B2 | 1/2007 | Cooney et al. | |
| 7,527,631 B2 | 5/2009 | Maroney et al. | |
| 7,604,665 B2 | 10/2009 | Iannotti et al. | |
| 7,608,109 B2 | 10/2009 | Dalla Pria | |
| 7,625,408 B2 | 12/2009 | Gupta et al. | |
| 2001/0011192 A1 | 8/2001 | Ondrla et al. | |
| 2001/0018589 A1 * | 8/2001 | Muller | 606/88 |
| 2001/0030339 A1 | 10/2001 | Sandhu et al. | |
| 2002/0082702 A1 * | 6/2002 | Resch et al. | 623/19.11 |
| 2002/0099445 A1 | 7/2002 | Maroney et al. | |
| 2003/0028253 A1 | 2/2003 | Stone et al. | |
| 2003/0045883 A1 * | 3/2003 | Chow et al. | 606/88 |
| 2003/0055507 A1 | 3/2003 | McDevitt et al. | |
| 2003/0065397 A1 | 4/2003 | Hanssen et al. | |
| 2003/0097183 A1 | 5/2003 | Rauscher et al. | |
| 2003/0114933 A1 | 6/2003 | Bouttens et al. | |
| 2003/0149485 A1 | 8/2003 | Tornier | |
| 2003/0187514 A1 | 10/2003 | McMinn | |
| 2004/0064189 A1 | 4/2004 | Maroney et al. | |
| 2004/0162619 A1 | 8/2004 | Blaylock et al. | |
| 2004/0193277 A1 | 9/2004 | Long et al. | |
| 2004/0193278 A1 | 9/2004 | Maroney et al. | |
| 2004/0220673 A1 | 11/2004 | Dalla Pria | |
| 2004/0220674 A1 | 11/2004 | Dalla Pria | |
| 2004/0230312 A1 | 11/2004 | Hanson et al. | |
| 2005/0021148 A1 | 1/2005 | Gibbs | |
| 2005/0125068 A1 | 6/2005 | Hozack et al. | |
| 2005/0171613 A1 | 8/2005 | Sartorius et al. | |
| 2006/0030946 A1 | 2/2006 | Ball et al. | |
| 2006/0069443 A1 | 3/2006 | Deffenbaugh et al. | |
| 2006/0069444 A1 | 3/2006 | Deffenbaugh | |
| 2006/0074353 A1 | 4/2006 | Deffenbaugh et al. | |
| 2006/0074430 A1 | 4/2006 | Deffenbaugh et al. | |
| 2006/0100714 A1 | 5/2006 | Ensign | |
| 2006/0161260 A1 | 7/2006 | Thomas et al. | |
| 2007/0219637 A1 | 9/2007 | Berelsman et al. | |
| 2007/0219638 A1 | 9/2007 | Jones et al. | |
| 2007/0225817 A1 | 9/2007 | Reubelt et al. | |
| 2008/0208348 A1 | 8/2008 | Fitz | |
| 2008/0234820 A1 | 9/2008 | Felt et al. | |
| 2009/0125113 A1 | 5/2009 | Guederian et al. | |
| 2009/0143865 A1 | 6/2009 | Hassler et al. | |
| 2009/0204225 A1 | 8/2009 | Meridew et al. | |
| 2009/0281630 A1 | 11/2009 | Delince et al. | |
| 2009/0312839 A1 | 12/2009 | Scheker et al. | |

FOREIGN PATENT DOCUMENTS

| | | |
|---|---|---|
| EP | 03/29854 B1 | 8/1989 |
| EP | 0339530 A2 | 11/1989 |
| EP | 05/38895 A2 | 4/1993 |
| EP | 05/38895 A3 | 4/1993 |
| EP | 0 903 127 A2 | 3/1999 |
| FR | 2653498 A1 | 4/1991 |
| FR | 2704747 A1 | 11/1994 |
| FR | 2776506 A1 | 10/1999 |
| WO | WO 01/34040 A1 | 5/2001 |
| WO | WO 02/067821 A2 | 9/2002 |
| WO | WO 02/067821 A3 | 9/2002 |
| WO | WO 03/005933 A2 | 1/2003 |
| WO | WO 03/005933 A3 | 1/2003 |
| WO | WO 03/030770 A2 | 4/2003 |

\* cited by examiner

INSTRUMENT FOR PREPARING AN IMPLANT SUPPORT SURFACE AND ASSOCIATED METHOD

TECHNICAL FIELD OF THE INVENTION

The present invention relates generally to the field of orthopaedics, and more particularly, to an implant for use in arthroplasty.

CROSS-REFERENCE TO RELATED APPLICATIONS

CROSS REFERENCE IS MADE TO THE FOLLOWING APPLICATIONS: U.S. patent application Ser. No. 10/951,023 entitled "EXTENDED ARTICULATION PROSTHESIS ADAPTOR AND ASSOCIATED METHOD", U.S. patent application Ser. No. 10/951,024 entitled "GLENOID AUGMENT AND ASSOCIATED METHOD", U.S. patent application Ser. No. 10/951,021 entitled MODULAR GLENOID PROSTHESIS AND ASSOCIATED METHOD", and U.S. patent application Ser. No. 10/951,022 entitled "GLENOID INSTRUMENTATION AND ASSOCIATED METHOD", filed concurrently herewith which are incorporated herein by reference.

BACKGROUND OF THE INVENTION

During the lifetime of a patient, it may be necessary to perform a total shoulder replacement procedure on the patient as a result of, for example, disease or trauma. In a total shoulder replacement procedure, a humeral component having a head portion is utilized to replace the natural head portion of the arm bone or humerus. The humeral component may include an elongated intramedullary stem which is utilized to secure the humeral component to the patient's humerus. In such a total shoulder replacement procedure, the natural glenoid surface of the scapula is resurfaced or otherwise replaced with a glenoid component that provides a bearing surface for the head portion of the humeral component. The humeral component may be made without a stem or with a short stem.

As alluded to above, the need for a shoulder replacement procedure may be created by the presence of any one of a number of conditions. One such condition is the deterioration of the patient's scapula in the glenoid surface as a result of, for example, glenohumeral arthritis. In such a condition, erosion of the patient's scapula may be observed. The erosion may be asymmetric, anterior or posterior. Posterior erosion of on the glenoid surface is particularly common. Such erosion of the scapula renders treatment difficult, if not impossible, with a conventional glenoid prosthesis.

In order to treat a condition in which a portion of the scapula has been eroded, a number of glenoid prostheses have heretofore been designed. Such glenoid prostheses, known generally as augmented glenoid prostheses, have a posterior edge that is thicker than the corresponding anterior edge.

In FIG. 1, a heretofore-designed augmented glenoid component 1 is shown. The glenoid component 1 has a metallic backing component 5 and plastic insert 4.

The thickness of the metallic backing component 5 gradually increases from an anterior edge to a posterior edge thereof. The arcuate-shaped medial surface 2 may over time lead to loosening of the augmented glenoid component 1, thereby potentially necessitating additional surgical procedures to replace or reseat the component 1. Further, due to the configuration of the medial surface 2, a relatively high shear load is created along the implant-to-bone interface when the component 1 is implanted. The presence of a high shear load along the implant-to-bone interface tends to also cause loosening of the component 1 over a period of time. Post-operative loosening is the largest cause of failures of implanted glenoid components.

As shown in FIG. 1, the metal backing may include additional features in the form of, for example, pegs 6 and center peg 7 to provide additional support of the glenoid implant on the scapula 3.

In FIG. 2 another heretofore-designed augmented glenoid component 8 is shown. The glenoid component 8 has a single component plastic body 9A. The thickness of the plastic body 9A gradually increases from an anterior edge 8A to a posterior edge 8B thereof thereby creating a relatively smooth, arcuate-shaped medial surface 10 from which a number of posts or pegs 8 extend. The design of this augmented glenoid component 8, however, suffers from at least the same drawbacks as the glenoid component 1.

In FIG. 3 another heretofore-designed augmented glenoid component 11 is shown. The glenoid component 11 also has a single component plastic body 11A. The thickness of the plastic body 9B gradually increases from an anterior edge 11A to a posterior edge 11B thereof thereby creating a relatively smooth medial surface 11C from which a keel 12 extends. The design of this augmented glenoid component 11, however, suffers from at least the same drawbacks as the glenoid components 1 and 8.

Attempts to correct the four mentioned problems with posterior glenoid wear have included the invention of an augmented glenoid component with a step support face with the step support face being posterior. Such an augmented glenoid component is much more fully described in U.S. Pat. No. 6,699,289 to Iannotti et al issued Mar. 2, 2004. Hereby incorporated in its entirety by reference.

The augmented glenoid component of U.S. Pat. No. 6,699,289 requires a stepped pocket or locating surface for the augmented glenoid component. Such a stepped surface is very difficult to create. Certain processes for preparing the glenoid fossa for such a component can consist merely of hand or power tools, which are manually guided to prepare the cavity for receiving the augmented glenoid component.

What is needed therefore is a surgical procedure and instrumentation to overcome one or more of the afore mentioned problems.

SUMMARY OF THE INVENTION

According to the present invention, an instrument and method for performing surgery is provided, which includes the careful preparation of the bone surface for preparing a posterior augmented glenoid. The present invention includes a device to produce a geometry of a complex nature for an implant surface when irregular bone loss has occurred and an augmented implant component is advised.

According to the present invention, a device and technique are provided by which the surgeon can mill the glenoid surface in a bone preserving fashion. A step is created in the glenoid fossa that replicates the backside surface of an augmented step glenoid implant such as that of U.S. Pat. No. 6,699,289. The instrumentation may include a rotating mill with a sleeve that has a fixed pivoting axis to create a cylindrical shape in the posterior aspect of the eroded glenoid fossa. This mill, with the pivoting axis, engages a guide that prescribes or limits the proper depth for the step. This guide can be instructed in many ways that permit the mill to plunge into the posterior glenoid and then pivot on its axis while milling the bone. The device is used to create a cylindrical step in the glenoid so that the glenoid implant can be fully supported.

This step glenoid of the glenoid implant and underlying bony support permits forces to be transmitted to the scapula in a manner that greatly reduces sheer. By reducing the risk of high sheer it is believed the implant will be more stable and less likely to result in loosening and failure.

According to the present invention, two distinct devices may work in concert to create a desired step geometry for the augmented step glenoid implant. The first of these devices is a milling device with a cutting head that embodies a specific shape matching the cross-sectional shape of the step portion of glenoid implant. The milling device is connected to a shaft for attachment to a power driven device such as a drill. Around the cutting head is a sleeve that has a pivoting axis at a specific position on the shaft such that when the cutting head is fully extended from the shaft, the cutting head is at a fixed known position relative to the pivoting axis. This permits a reproducible cylindrical geometry to be milled into the bone. Alternatively, the cutting head and sleeve may not move relative to each other and the cutting head may be in a fixed relationship with the pivoting axis on the sleeve.

The other device is a positioning jig that permits the surgeon to accurately place in a reproducible manner the milling device such that the mill removes only the bone necessary to match a glenoid implant to the patients condition. This jig defines a depth of cut as well as accurately positioning the cutter so that the device mills the bone longitudinally along the axis of the glenoid fossa. Only the posterior eroded bone is resurfaced to a defined shape matching the implant. The jig may accomplish this task while only permitting the rotation of the pivoting axis defined on the mill sleeve. The translation of the mill device may be permitted in a medial lateral direction. An end stop defines the depth of the step relative to the reamed anterior portion of the glenoid fossa.

The two devices function together to create a reproducible geometry on the glenoid where posterior bone loss exists permitting the use of a posterior augmented glenoid implant.

According to one embodiment of the present invention, there is provided an instrument for preparing a surface of a joint. The surface is adapted for receiving a prosthesis component having a feature closely conforming to the surface. The prosthesis component provides a bearing surface for a portion of a long bone. The instrument includes a guide having a first feature and a second feature and a tool. The tool is used for cooperation with the first feature for preparing the surface. The first feature is adapted to at least partially control the position of the tool as it prepares the surface. The second feature is adapted to assist in positioning of the guide with respect to the joint.

According to another embodiment of the present invention there is provided an instrument for preparing a feature on a scapula. The feature is adapted for receiving an augmented glenoid component for providing a bearing surface for a head portion of a humerus. The instrument includes a guide defining a guiding feature and a locating feature and a tool. The tool is used for cooperation with the guiding feature for preparing the feature. The guiding feature is adapted to at least partially guiding the tool as it prepares the glenoid surface. The locating feature is adapted to assist in locating the guide with respect to the scapula.

According to still another embodiment of the present invention there is provided an instrument kit for use in preparing a glenoid of a scapula. The glenoid is adapted for receiving glenoid component having a feature closely conforming to the glenoid. The glenoid component provides a bearing surface for a head portion of a humerus. The instrument kit includes a first portion tool for preparing a first portion of the glenoid of a scapula and a second portion tool assembly for preparing a second portion of the glenoid of a scapula. A substantial portion of the second portion tool is spaced from the first portion.

According to a further embodiment of the present invention, there is provided a method for performing arthroplasty on a glenoid. The method includes the steps of determining a reference location on the glenoid and preparing a location feature in the glenoid corresponding to the reference location. The method also includes the steps of providing a cutting guide, securing the cutting guide to the location feature, and providing a cutter. The method also includes the steps of preparing a cavity in the glenoid with the cutter, using the cutting guide to at least partially control the position of the cutter as it prepares the cavity. The method further includes the steps of providing a glenoid implant and implanting the glenoid implant onto the cavity.

The technical advantages of the present invention include the ability to reproduce the complex geometry in a glenoid to replicate and support a posterior augmented glenoid. For example, according to one aspect of the present invention, an instrument kit for preparing a glenoid scapula is provided. The glenoid is adapted for receiving a glenoid component having a feature closely forming to the glenoid. The glenoid component provides a bearing surface for a head portion of a humerus.

The instrument kit includes a first portion tool for preparing a first portion of the glenoid and a second portion of the glenoid. A substantial portion of the second portion is spaced from the first portion. The second portion tool assembly includes a guide having a first feature and a second feature and a second portion tool. The second portion tool cooperates with a first feature for preparing the second portion of the glenoid. The first feature is adapted to at least partially to control the position of the second portion of the tool as prepares the second glenoid surface. The guide and tools provides a reproducible complex geometry. Thus, the present invention provides for a reproducible complex geometry and a glenoid to replicate and support the posterior augmented glenoid.

The technical advantages of the present invention, further include the ability to produce a support surface to support a glenoid that transmits forces normally to the articulating surface. The normal support results in less shear, greater stability and less likelihood of the glenoid prosthesis to loosen. For example, according to another aspect of the present invention, an instrument kit is provided with a first portion tool for preparing a first portion of the glenoid and a second portion tool for preparing a second portion of the glenoid. The second portion tool cooperates with the first feature prepared by the first portion tool. The guide includes a base and a restraining component to guide the tool in a position normal to the articulating surface. Thus, the present invention provides for a support surface to support a glenoid that transmits forces normally to the articulating surface.

The technical advantages of the present invention further include the ability to remove only bone that is necessary to match the implant. For example, according to yet another aspect of the present invention, an instrument kit is provided for preparing a glenoid of a scapula including a first portion tool for preparing a first portion of the glenoid and a second portion tool assembly. The second portion tool assembly is supported by the surface prepared by the first portion tool. The second portion tool assembly includes a rotatable tool and a cylindrical tube surrounding the tool. The cylindrical tube is pivotally attached to a bearing to provide a shape similar to that of the posterior augmented portion of the posterior augmented glenoid. Thus, the present invention provides for the removal of only the bone necessary to match the implant.

The technical advantages of the present invention, further include the ability of the jig to define the depth of cut for preparing the glenoid surface. For example, according to one aspect of the present invention, an instrument kit is provided including a first portion tool for preparing a first portion and a second portion tool assembly including a guide supported by the surface prepared by the first portion tool and a second portion tool for cooperating with the guide. The guide and the second portion tool act in concert to define the depth of cut. Thus, the present invention provides for a jig that can define the depth of cut.

The technical advantages of the present inventions further include the ability of the instrument to accurately position the cutter. For example, according to yet another aspect of the present invention, an instrument kit is provided with a first portion tool and a second portion tool assembly including a guide supported by the surface prepared by the first portion tool. The second portion tool assembly includes a guide having a base and a restraining component. The restraining component restrains the second portion tool to provide for an accurate position of the cutter. Thus, the present invention provides for a guide for accurately positioning the cutter.

The technical advantages of the present invention, further include the ability of the instrument of the present invention to be used for right and left hand shoulders. For example according to a further of the present invention, the instrument kit includes a guide, which may be symmetrically designed. By being symmetrically designed, the guide may be used for both right and left-hand shoulders. Thus, the present invention, provides for an instrument that can be used for right and left hand shoulders.

The technical advantages of the present invention, further include the ability of the instrument to be used for all sizes and shapes of glenoid implants. For example, according to yet another aspect of the present invention, the instrument includes a first portion tool for preparing a first portion of the glenoid and a second portion tool including a guide being supported by the surface prepared by the first portion tool and a second portion tool to be constrained by the guide. The guide may be modular or may include an internal component or bushing to provide for different diameters of the second portion tool. Similarly, the first portion tool may be provided with different sizes to provide for a variety of glenoid implants. Thus, the present invention provides for an instrument that may be used for all sizes of glenoid implants.

Other technical advantages of the present invention will be readily apparent to one skilled in the art from the following figures, descriptions and claims.

BRIEF DESCRIPTION OF THE DRAWINGS

Corresponding reference characters indicate corresponding parts throughout the several views. Like reference characters tend to indicate like parts throughout the several views.

DETAILED DESCRIPTION OF THE INVENTION

Figure 1:
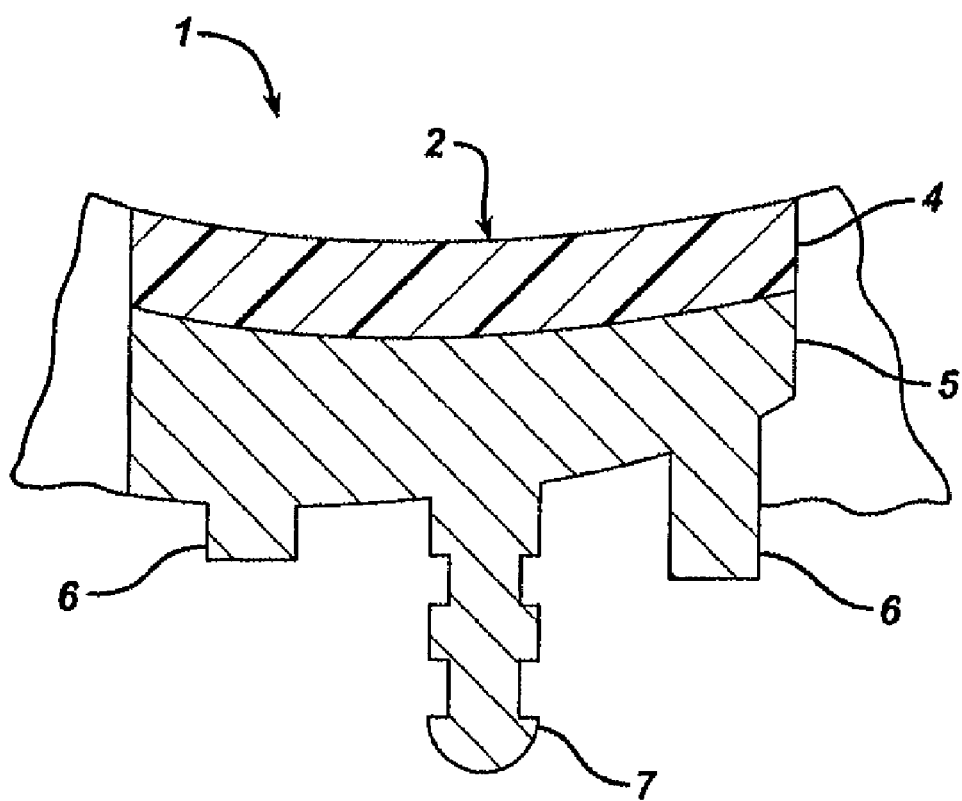
FIG. 1 is a side sectional view of a prior art augmented glenoid component.
Figure 2:
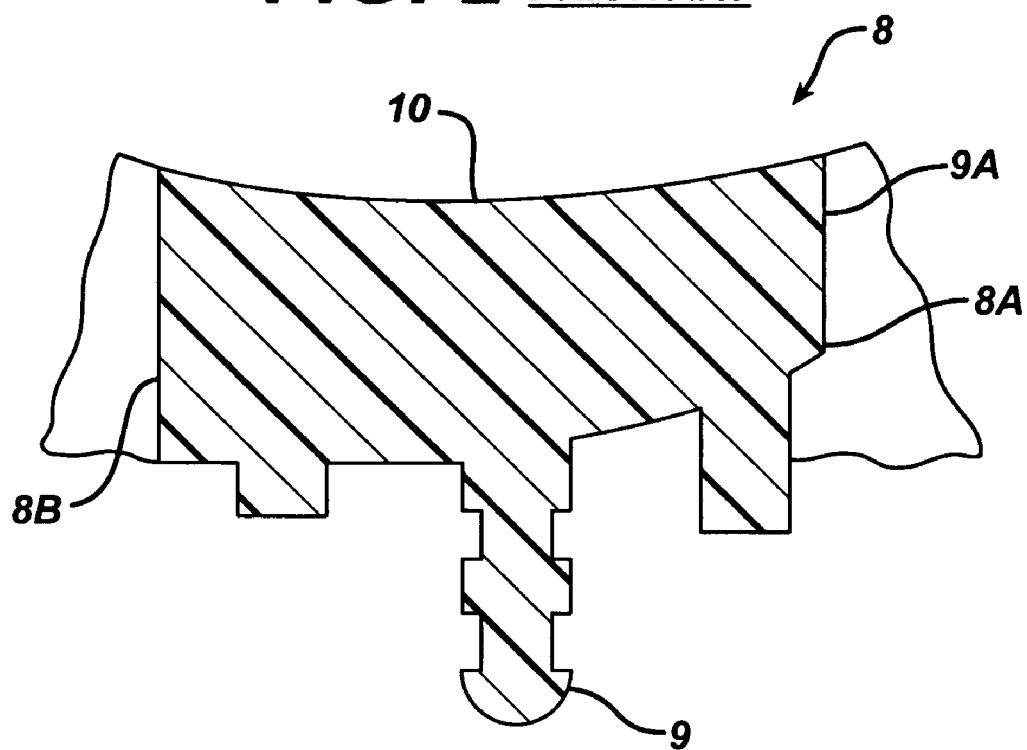
FIG. 2 is a side sectional view of another prior art augmented glenoid component.
Figure 3:
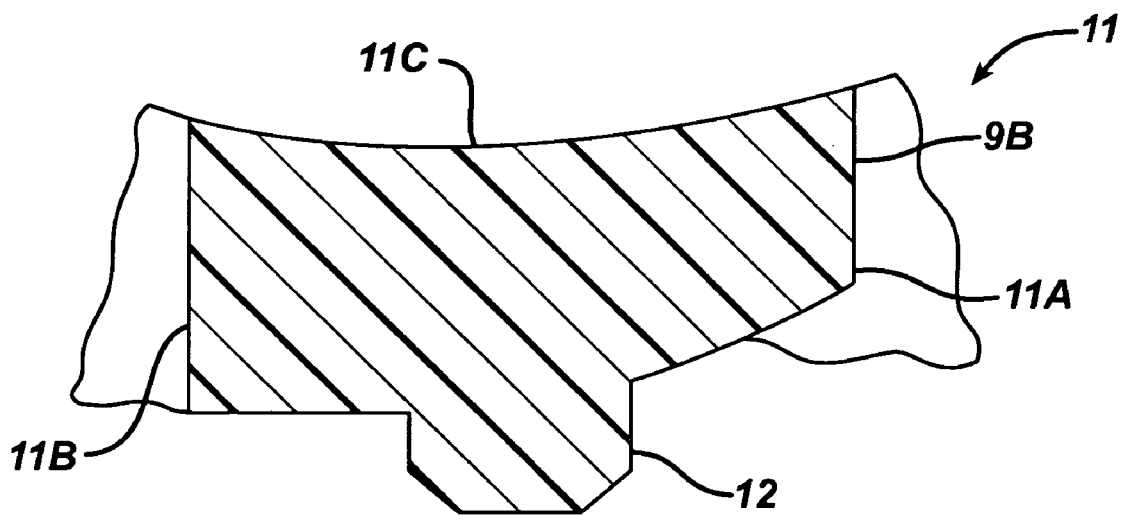
FIG. 3 is a side sectional view of another prior art augmented glenoid component.
Figure 4:
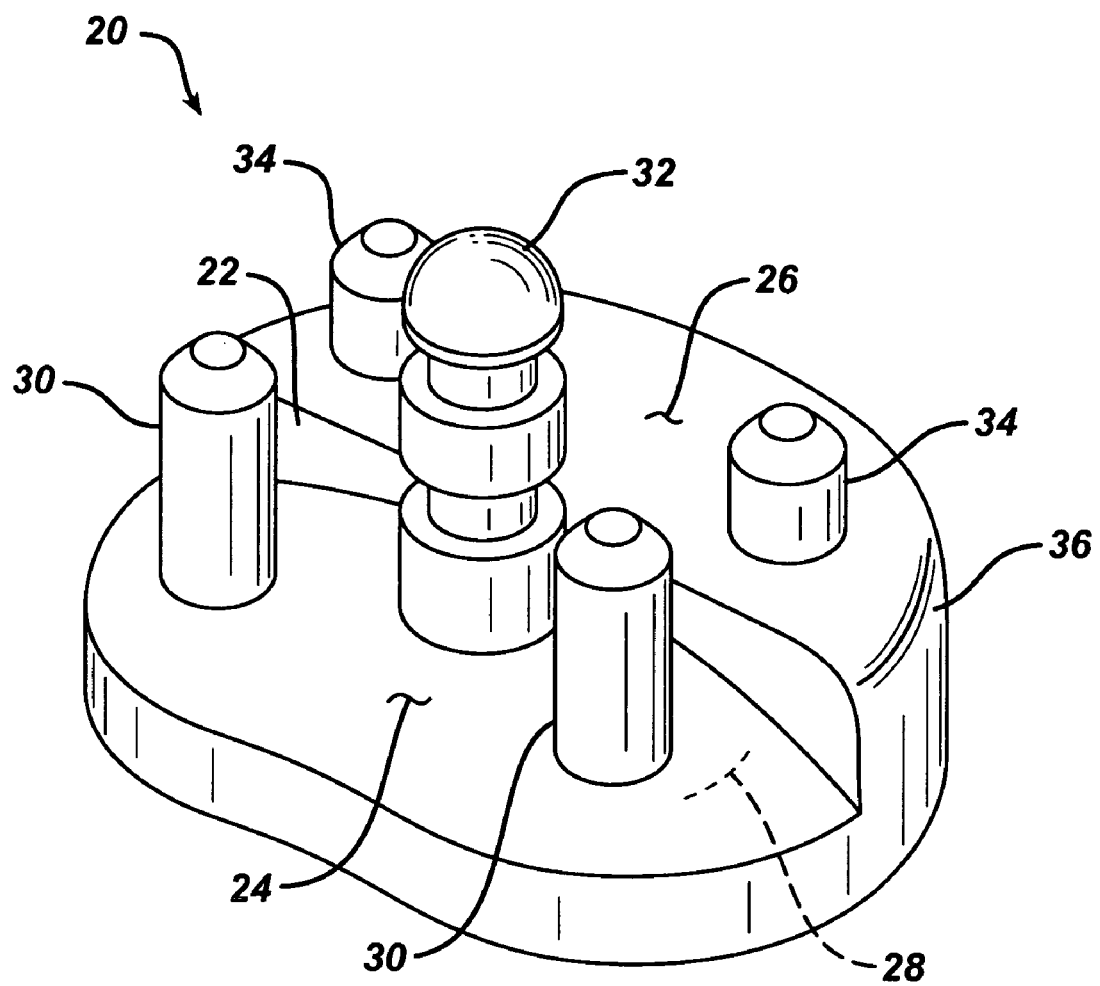
FIG. 4 is a perspective view showing an augmented glenoid component for use in a cavity prepared by the cutting tool of the present invention.
Figure 5:
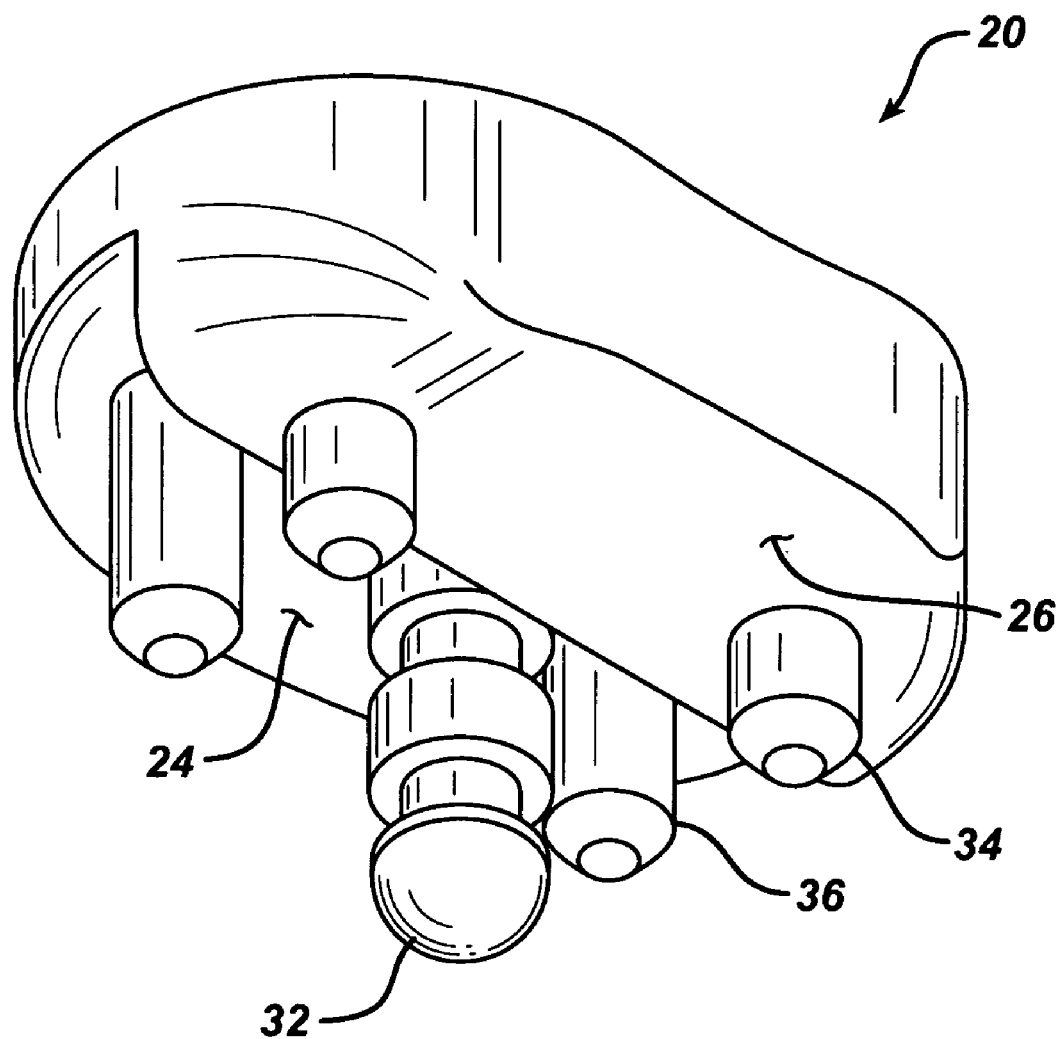
FIG. 5 is another perspective view of the augmented glenoid component of FIG. 4.
Figure 6:
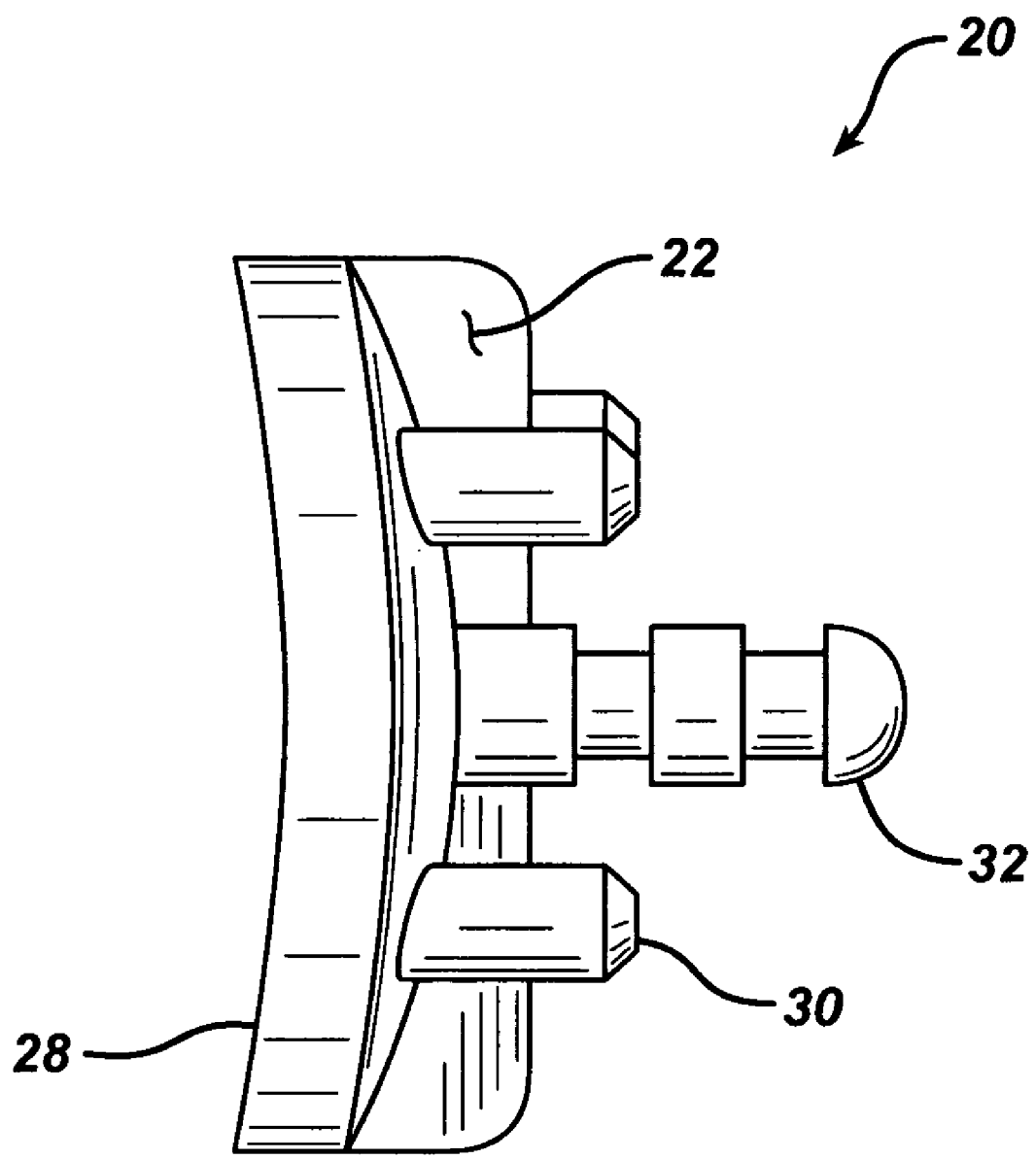
FIG. 6 is an end view of the augmented glenoid component of FIG. 4.
Figure 7:
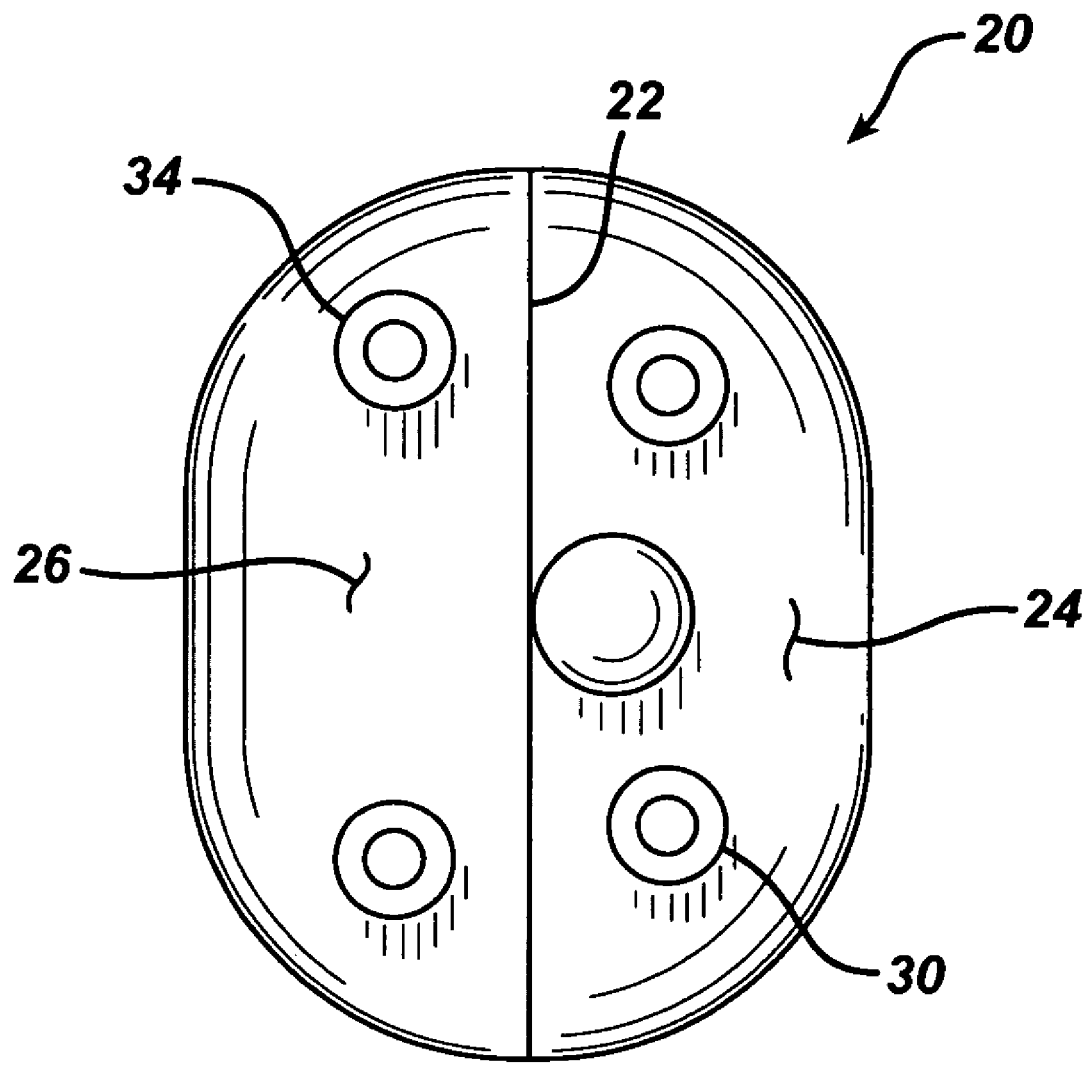
FIG. 7 is an bottom view of the augmented glenoid component of FIG. 4.
Figure 8:
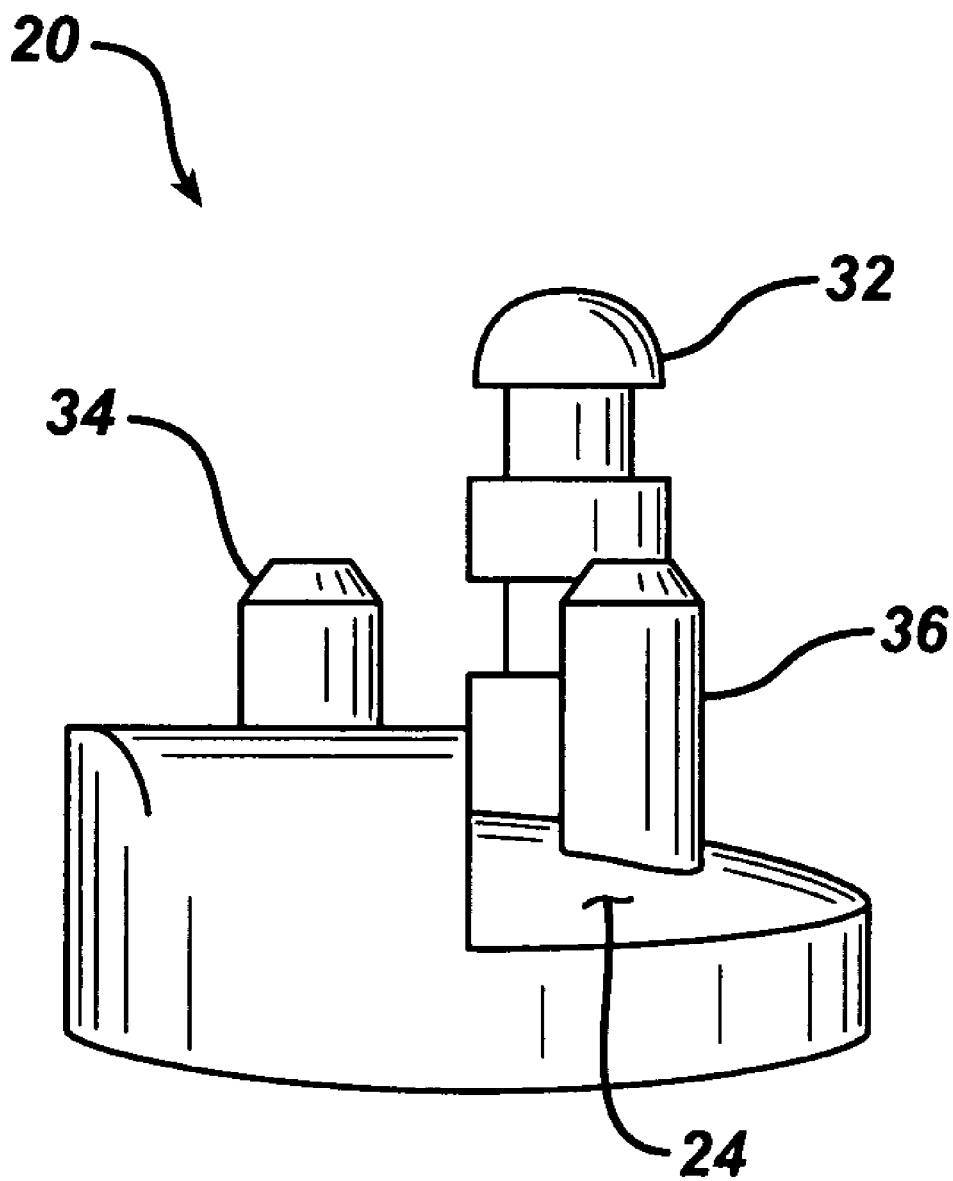
FIG. 8 is an side view of the augmented glenoid component of FIG. 4.

Embodiments of the present invention and the advantages thereof are best understood by referring to the following descriptions and drawings, wherein like numerals are used for like and corresponding parts of the drawings.

Referring now to FIG. 4-8, the glenoid component 20 is shown, which may be used in the cavity prepared by the instrument of the present invention. The glenoid component 20 is in the form of an augmented glenoid and may, as shown in FIG. 4-8 include a buttress 22 separating a first mounting surface 24 from a second mounting surface 26. The glenoid component 20 may include an articulating surface 28 positioned opposed to the mounting surfaces 24 and 26.

The augmented glenoid component 20 may include additional features to help secure the glenoid component 20 to the scapula. For example, the first mounting surface 24 may include first pegs 30 extending from the mounting surface 24 as well as a central peg 32. The second mounting surface 26 may also include pegs 30 for extending from the mounting surface 26. The second mounting surface and the articulating surface 28 define a posterior augment 36 positioned between the mounting surface 26 and the articulating surface 28. The posterior augment 36 provides support for the posterior erosion of the glenoid.

Figure 9:
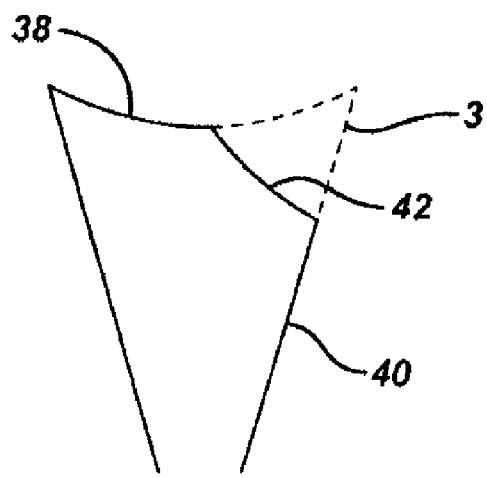
FIG. 9 is a side view partially in cross section of a natural glenoid fossa with posterior erosion.

Referring now to FIG. 9, natural glenoid 38 of scapula 40 is shown. The natural glenoid 38 includes a portion 3 of the scapula 40 with a surface 42 describing posterior erosion.

Figure 10:
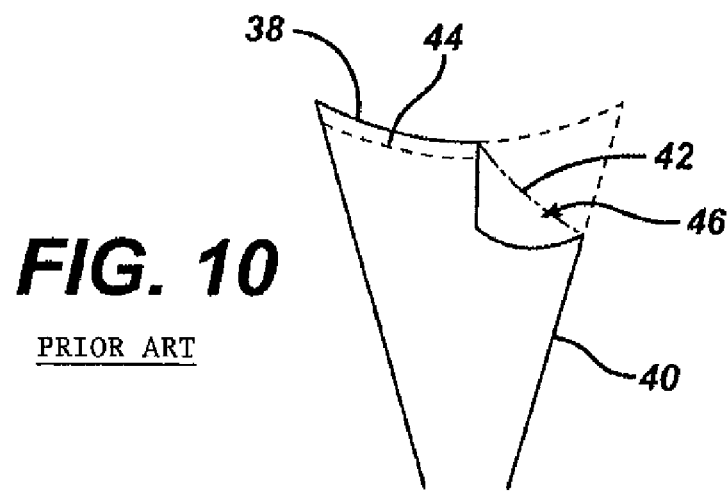
FIG. 10 is a side view partially in cross section of a natural glenoid fossa with a portion machined for receiving a prior art glenoid component.

Referring now to FIG. 10, the scapula 40 is shown with a first milled surface 44 extracted from the natural glenoid 38 and a pocket 46 machined with the instruments of the present invention shown removing the posterior erosion surface 42. The machined glenoid surface 44 and the pocket 46 may be prepared utilizing the instruments of the present invention.

Figure 11:
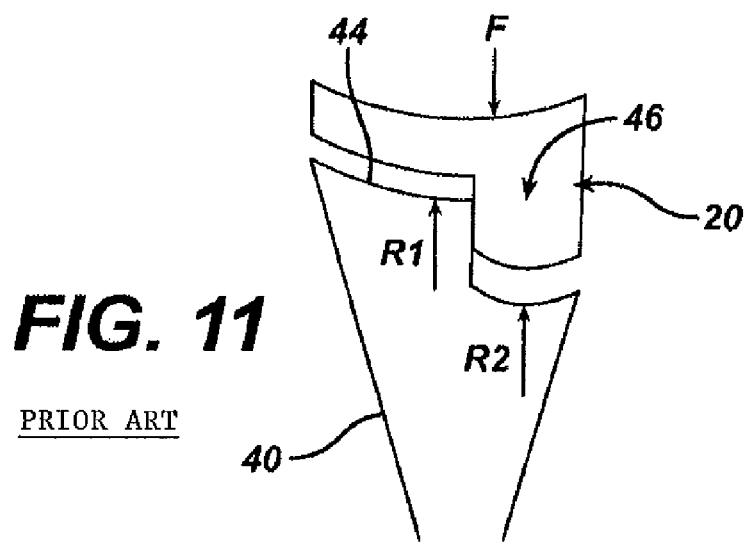
FIG. 11 is a side sectional view of a prior art augmented glenoid component in position on a prepared glenoid fossa.

Referring now to FIG. 11, the glenoid component 20 of FIGS. 4-8 is shown in position above on the pocket 46 and glenoid surfaces 44 prepared by the instruments of the present invention. As can be shown in FIG. 11, the force F from the patient may be supported by resistance forces R1 and R2 extending from the prepared glenoid surface 44 and the pocket 46 respectively. As can be seen in FIG. 11, the forces R1, R2, and F are all collinear. Thus, the instrument of the present invention provides for a posterior augmented glenoid 20, which provides for normal forces and minimizes shear forces to provide for less shear and a more stable glenoid implant that is less likely to loosen during use.

Figure 12:
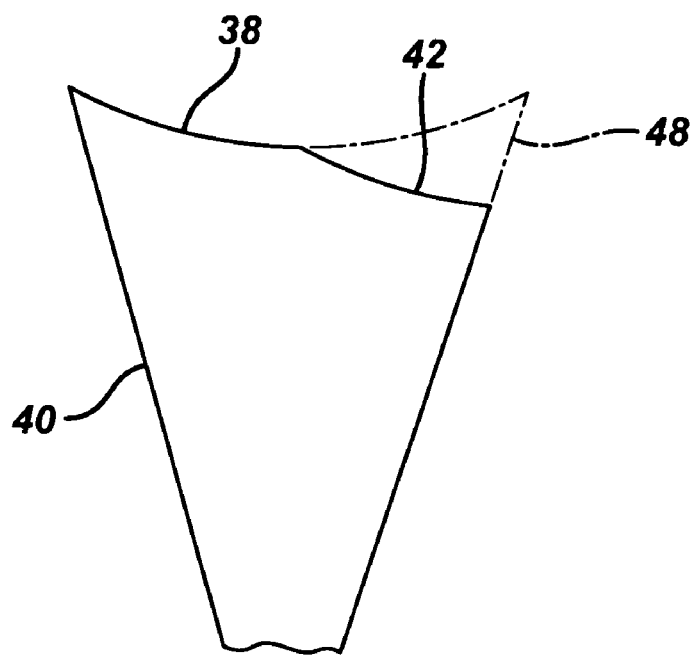
FIG. 12 is a side view partially in cross section of another natural glenoid fossa with posterior erosion.

Referring now to FIG. 12, a glenoid fossa of a scapula 40 is shown. The glenoid fossa 38 includes a posteriorly eroded surface 42 with the healthy glenoid surface shown in phantom as surface 48.

According to the present invention and referring now to FIG. 13-19, instrumentation and a corresponding method are shown for preparing an implant support surface for a glenoid implant.

Figure 13:
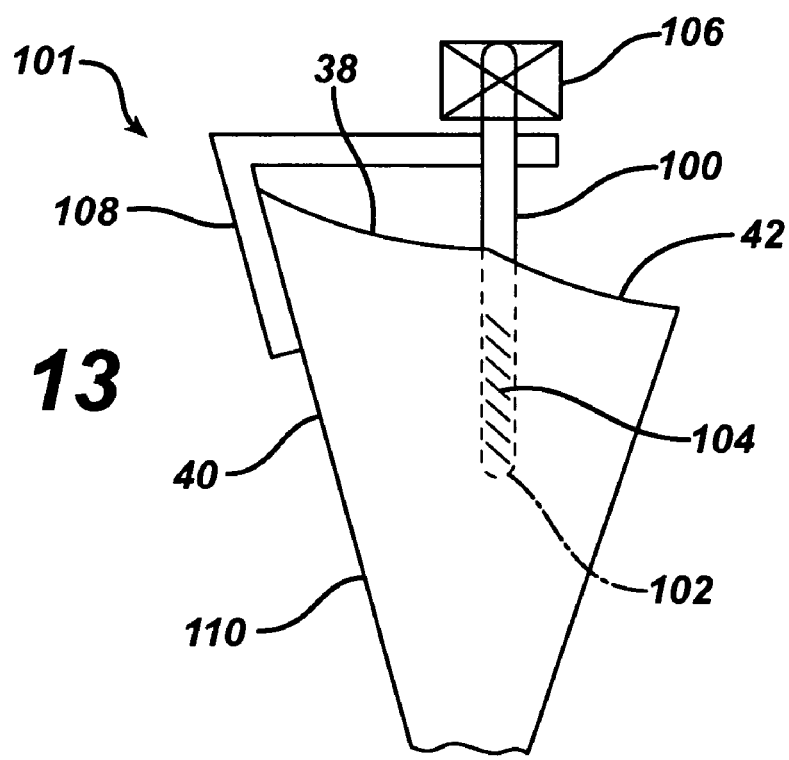
FIG. 13 is a side view partially in cross section of the natural glenoid fossa with posterior erosion of FIG. 12 with an alignment pin in position in the glenoid.

According to the present invention and referring now to FIG. 13, an alignment pin 100 is shown in position in the scapula 40. The alignment pin 100 may include, for example, a point or cutting edge 102 for use in cutting bone in the installation process of the alignment pin 100. The alignment pin 100 may further include external threads 104 for assisting in the insertion of the alignment pin 100. The alignment pin 100 may be a part of an instrument set 101.

The alignment pin 100 may be positioned in the glenoid fossa 38 of the scapula 40 in any suitable manner. For example, the alignment pin 100 may be manually inserted. The alignment pin may be inserted by hand or with the use of, for example, a power tool, for example, a drill 106. The alignment pin 100 may be positioned manually or may as shown in FIG. 13, may be guided by, for example, guide 108 that is positioned against outer surface 110 of the scapula 40. It should be appreciated that that alignment pin 100 may be inserted using diagnostic techniques such that using a fluoroscope or may alternatively be positioned using computer aided surgical devices. For example, and as shown in FIG. 13 the alignment pin 100 may be centrally positioned in the glenoid fossa 38. The guide 108 and the drill 106 may also be part of the instrument set 101.

Figure 14:
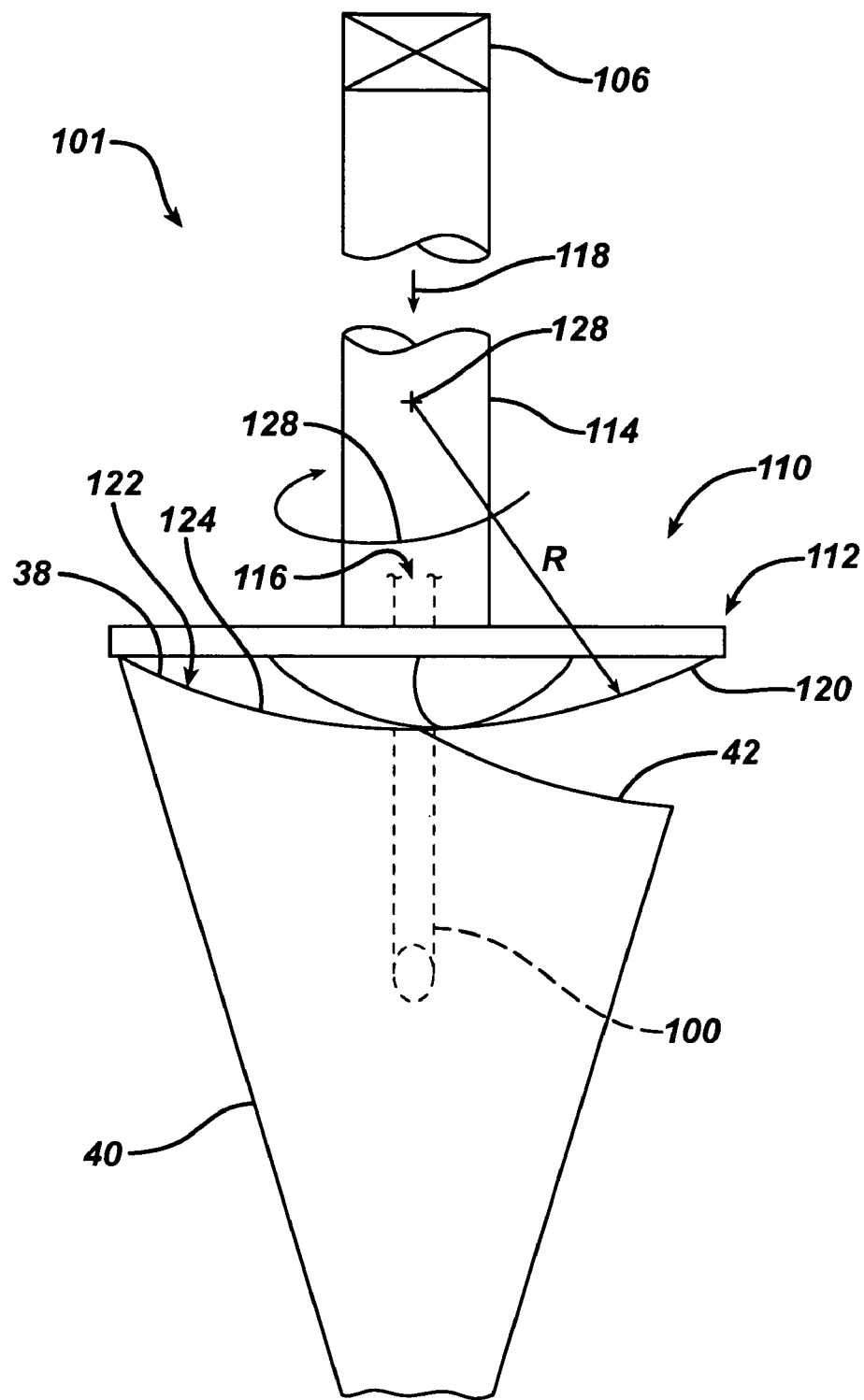
FIG. 14 is a side view partially in cross section of the natural glenoid fossa with posterior erosion with an alignment pin of FIG. 13 showing an end mill in contact with the glenoid fossa preparing a surface according to an embodiment of the present invention.

According to the present invention and referring now to FIG. 14, a first portion tool 110 in the form of, for example, an end mill is shown. The end mill 110 includes a cutter 112 to which shank 114 is attached. The end mill 110 includes the central opening 116. The central opening 116 is sized for sliding engagement with alignment pin 100. The end mill 110 may also be part of the instrument set 101.

As shown in FIG. 14, the end mill 110 is positioned above the glenoid fossa 38 and the alignment pin 100 is engaged with opening 116 to advance the end mill 110 in the direction of arrow 118 until cutting edge 120 of the cutter 112 engages with the glenoid fossa 38. The cutting edge 120 is utilized to form first portion 122 of prepared surface 124. The first portion 122 of the prepared surface 124 may have any shape. For example, and as is shown in FIG. 14, the first portion 122 of the prepared surface 124 may have a shape defined by cutting edge 120 of the cutter 112. While the cutter 112 may have any suitable shape, for simplicity and is shown in FIG. 14, the cutter 112 has a cutting edge 120 defined by a radius R extending from origin 126. The cutting edge 120 thus is convex and may be, as shown in FIG. 14, a portion of a sphere. When machined by the cutting edge 120 of the cutter 112 of FIG. 14, the first portion 122 is generally concaved.

The end mill 110 may be manually rotated in the direction of arrow 128 by any suitable method. For example, the end mill 110 may be manually rotated or rotated by a tool in the form of, for example, a drill 106. Preferably and is shown in FIG. 14, the glenoid fossa 38 of the scapula 20 is machined until the entire concave portion 122 is a prepared surface.

Figure 15:
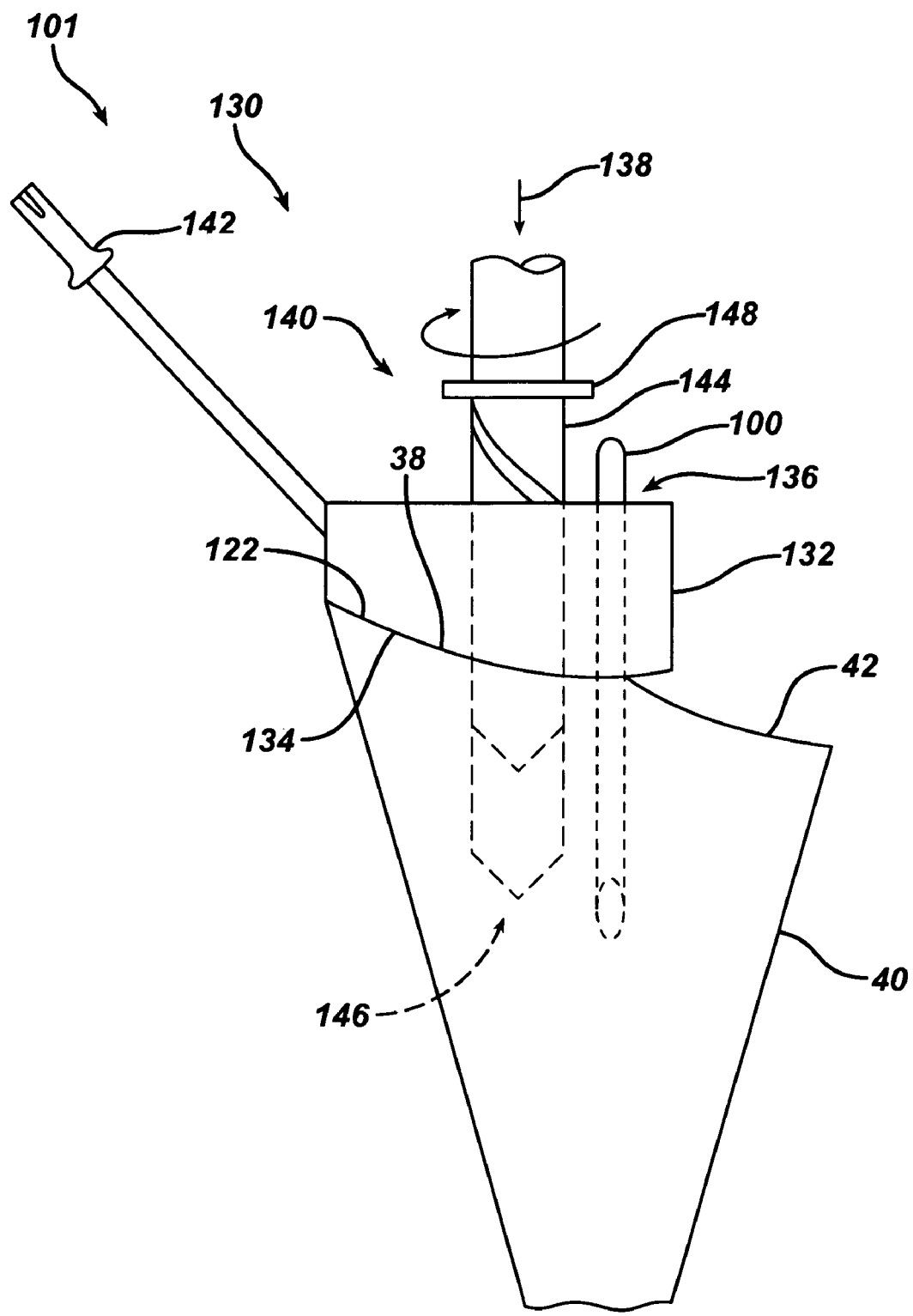
FIG. 15 is a side view partially in cross section of the glenoid fossa with posterior erosion showing the surface prepared by the end mill of FIG. 14 and showing a drill guide for preparing a glenoid component peg hole according to an embodiment of the present invention in position on the surface prepared by the end mill of FIG. 14.

According to the present invention and referring now to FIG. 15, a guide in the form of first drill guide 130 is shown as part of the instrument set 101 of the present invention. The first drill guide 130 is utilized after the concave first portion 122 has been prepared by the first portion tool 110 of FIG. 14.

The first drill guide 130 includes a base 132 having a contact surface 134 for contact with the prepared surface 122 of the scapula 40. The locating surface 134 preferably has the shape closely conform with the prepared surface 122. Thus, the contact surface 134 is preferably generally convex.

As shown in FIG. 15, the first drill guide 130 further may include an opening 136 for cooperation with alignment pin 101. The opening 136 is sized for slideably fitting the alignment pin 100. First drill guide 130 is installed onto the scapula 40 by advancing the first drill guide 130 in the direction of arrow 138 until the opening 136 of the base 132 is in alignment with alignment pin 100 with which the first drill guide 130 is thereby aligned. The alignment pin 100 is slidably fitted to opening 136 of the first drill guide 130. The first opening 136 of the drill guide 136 is then mated with the alignment pin 100 until convex surface 134 of the base 132 is seated against the prepared surface 122 of the scapula 40. In this position the first drill guide 130 is seated in location for its use.

The first drill guide 130 further includes a guiding feature 140 in the form of, for example, bushing or opening for receiving a drill. It should be appreciated and shown in FIG. 15, that the first drill guide 130 may include a handle 142 for assisting in the proper positioning of the first drill guide 130 against the scapula 40.

After the first drill guide 130 is in position against the scapula 40, a first peg tool 144 in the form of, for example, a drill is fitted into drill guide 140 and advanced downwardly in the direction of arrow 138 forming first peg opening 146 in the scapula 40. A stop 148 may be positioned on the drill 144 for seating against the base 132 to limit the downward motion of the drill 144 and thus set the proper depth for the opening 146.

Once the opening 146 has been prepared in the scapula 40, the first drill guide 130 may be removed from the glenoid fossa 38. At this point alignment pin 100 may also be removed from the glenoid fossa 38.

Figure 16:
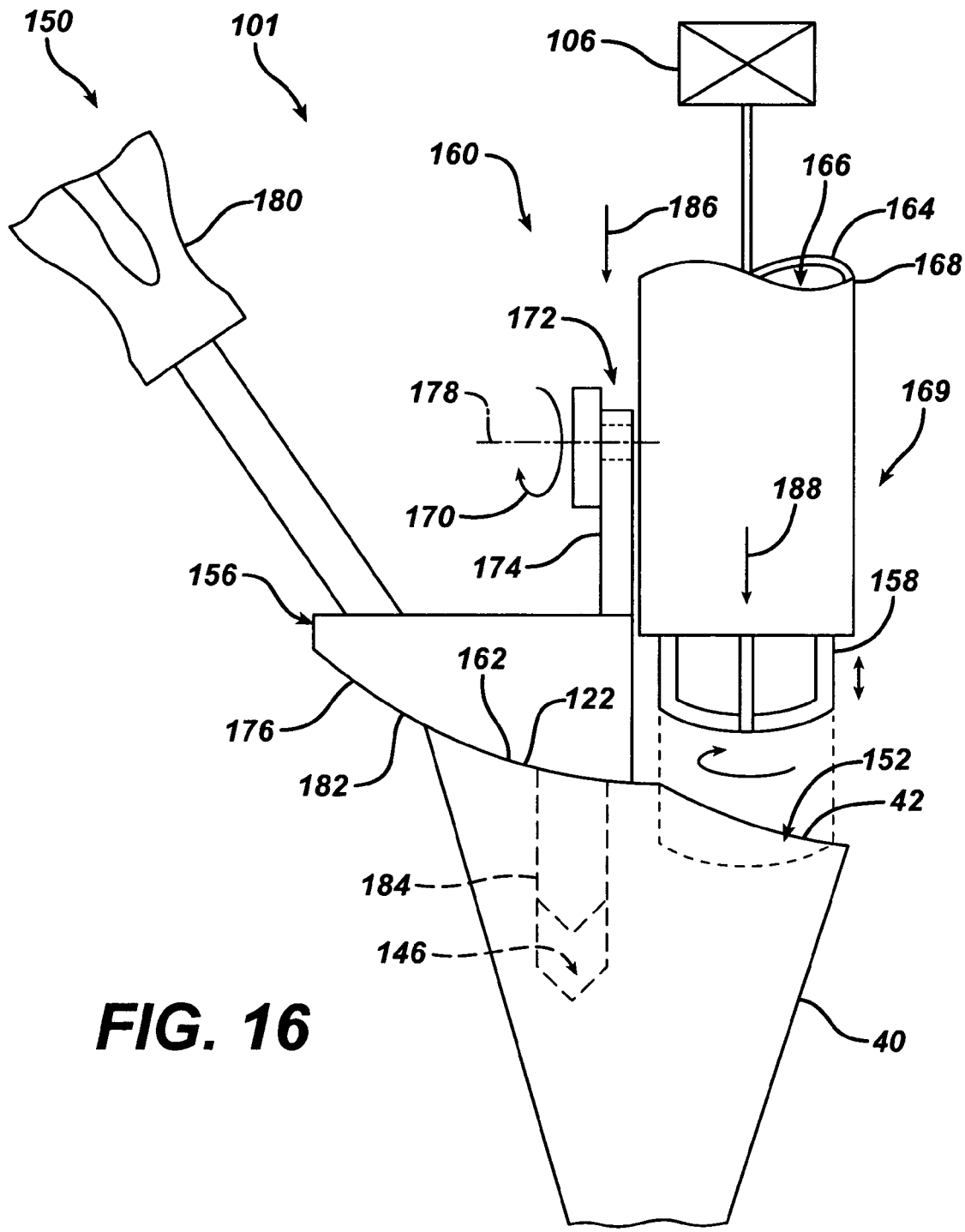
FIG. 16 is a side view partially in cross section of the glenoid fossa with posterior erosion showing cutting guide for use in preparing a mounting pocket for a posterior augmented glenoid component with the drill guide aligned to the peg hole prepared by the drill guide of FIG. 15 according to an embodiment of the present invention.

According to the present invention and referring now to FIG. 16, the instrument set 101 of the present invention may further include an instrument 150 for preparing a mounting pocket 152 posteriorly in the scapula 40. The posterior pocket preparing instrument 150 as shown in FIG. 16 includes a guide in the form of cutting guide 156 as well as, a tool in the form of, as shown in FIG. 16, of a milling cutter 158. The instrument 150 is utilized to prepare the glenoid surface or mounting pocket 152 of the scapula 40. The glenoid surface or mounting pocket 152 is adapted for receiving a glenoid component having a feature closely conforming to the glenoid surface. The glenoid component may be for example, glenoid component 20, as shown in FIGS. 4-8, and may provide a bearing surface for the head portion of a humerus.

The cutting guide 156 includes a first feature 160 in the form of a guiding feature adapted to at least partially control the position of the tool 158 as it prepares the mounting pocket 152. As shown in FIG. 16, the cutting guide 156 further includes the second feature 162. The second feature 162 is adapted to assist in positioning of the cutting guide 156 with respect to the scapula 40.

The first feature or guiding feature 160 may have any suitable size, shape and configuration for guiding the tool 158 to prepare the mounting pocket 152. For example and as is shown in FIG. 16, the guiding feature 160 may be defined by a wall 164 in the guiding feature for forming a cylindrical opening 166. The wall 164 may form a hollow cylinder 168. Alternatively, the wall 164, the opening 166, and cylinder 168 may constrain the tool or the cutter 158.

The first feature or guiding feature 160 may be moveable with respect to the cutting guide 156. For example, the cylinder 168 as shown in FIG. 16 may rotate relative to the cutting guide 156 in the direction of the arrows 170.

The guiding feature or first feature 160 may as shown in FIG. 16, include a bearing 172. The bearing 172 may include a post 174 extending outwardly from base 176, of the cutting guide 156. The bearing 172 may be in the form of a journal bearing or in the form of a trunnion. The cylinder 168 may pivot about the bearing 172 to prepare the mounting pocket 152.

The bearing 172 may define a bearing centerline 178 about which the tool 158 is pivotally attached. The centerline 178 may, as shown in FIG. 16, be generally parallel to the base 176. As shown in FIG. 16, the cutting guide 176 may further include a handle 180 for supporting and guiding the cutting guide 156.

The second feature or position feature 162 may have any suitable shape or form capable of positioning the cutting guide 156 with respect to the scapula 40. For example and is shown in FIG. 16, the cutting guide 156 may include a mounting surface 182 formed in base 176 of the cutting guide 156. The mounting surface 182 preferably and is shown in FIG. 16, has a shape compatable with the prepared surface 122 of the scapula 40. For example and is shown in FIG. 16, the mounting surface 182 is generally convex and may, for example, have a generally hemispherical shape.

The positioning feature 162 may in addition to the mounting surface 182 include a protrusion in the form of, for example, a pin 184. The pin 184 extends outwardly from mounting surface 182 of the base 176 of the cutting guide 156. The pin 184 may be generally cylindrical and adapted for a sliding fit within opening or peg hole 146 formed in the scapula 40.

The cutting guide 156 is installed by grasping the handle 180 and advancing the cutting guide 156 toward the scapula 40 in the direction of arrow 186. The pin 184 is aligned with peg hole 146 and the cutting guide 156 is advanced until the mounting surface 182 sits against prepared surface 122 of the scapula. Once the cutting guide 186 sits in position, the tool in the form of, for example, milling cutter 158, is advanced toward the scapula 40 in the direction of arrow 188 until the milling cutter 158 is in a full depth position. After the milling cutter 158 is at its full depth, the milling cutter 158 is rotated about bearing 172 in the direction of arrows 170 about axis 178 until the mounting pocket 152 is fully prepared. After the mounting pocket 152 is fully prepared, the cutting guide 156 is removed from the scapula 40.

The tool or milling cutter 158 may be rotated by any suitable method for example, milling cutter 158 may be manually rotated, or preferably, may be rotated by use of a power tool, for example, by drill 106.

Figure 17:
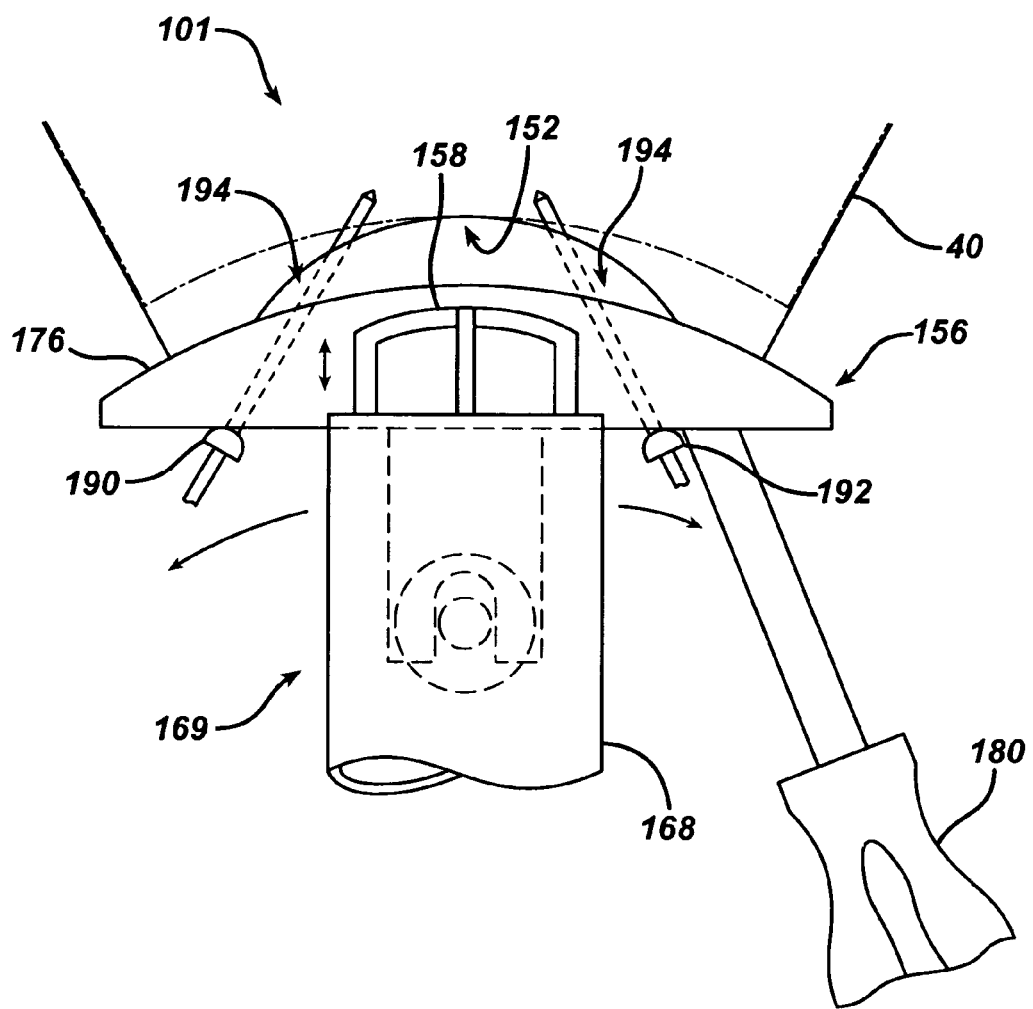
FIG. 17 is an end view of the cutting guide and glenoid fossa of FIG. 16.

Referring now to FIG. 17, it should be appreciated that cutting guide 156 may be further secured by additional features to secure the cutting guide 156 to the scapula 40. For example and is shown in FIG. 17, mounting screws, for example, first mounting screw 190 and second mounting screw 192 may be secured through openings 194 in the base 176 of the cutting guide 156. The mounting screws 190 and 192 are used to avoid requiring the holding of the cutting guide 156 in place manually while the mounting pocket 152 is prepared.

Figure 18:
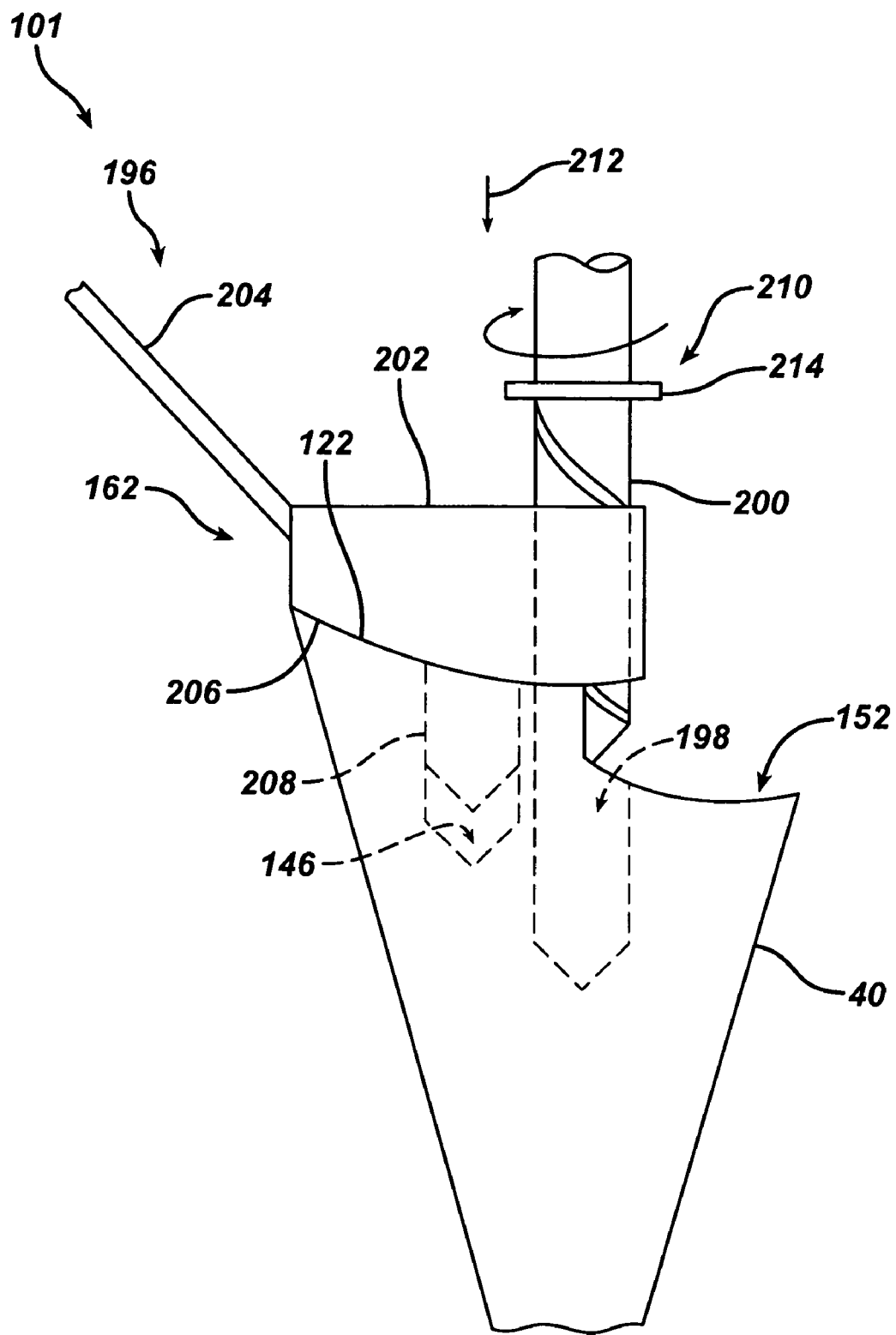
FIG. 18 is a side view partially in cross section of the glenoid fossa with posterior erosion showing the mounting pocket prepared using the cutting guide of FIG. 16 and showing a second drill guide for preparing a second glenoid component peg hole according to an embodiment of the present invention in position on the surface prepared by the end mill of FIG. 9.

Referring now to FIG. 18, optional features may be prepared in the scapula 40 for preparing the scapula 40 for receiving the glenoid implant for example, glenoid implant 20 of FIGS. 4-8. For example and is shown in FIG. 18, a second drill guide 196 may be utilized as a part of the instrument set 101. The second drill guide 196 is used to prepare second peg hole 198 for receiving the second peg (not shown) of the glenoid component 20 of FIGS. 4-8.

The second drill guide 196 may have any suitable size, shape, and configuration capable of guiding a tool, for example, a second drill 200 for preparing the second peg 198. The second drill guide 196 may, for example, include a base 202 and may include a handle 204 extending from the base 202 for assisting in positioning and securing the second drill guide 196 against the scapula 40.

The second drill guide 196 may include a positioning feature 162 in the form of, for example, mounting surface 206. The mounting surface 206 may be formed on base 202. The mounting surface 206 is adapted for positioning the base 202 against prepared surface 122 of the scapula 40. The mounting surface 206 is preferably closely conforming to the prepared surface 122 and may, as shown in FIG. 18, be generally convex. The mounting surface 206 may, as shown in FIG. 18, be generally hemispherical.

The positioning feature 162 of the second drill guide 196 may further include a peg hole alignment feature in the form of, for example, a peg hole alignment pin 208. The peg hole alignment pin 208 may be generally cylindrical in shape for close conformance to first peg hole 146 formed in the scapula 40.

The second drill guide 196 may further include a guiding feature 210 used in guiding the second drill 200 when preparing the second peg hole 198. The guiding feature 210 may as shown in FIG. 18, be in the form of a bushing or a cylindrical opening formation base 202 of the drill guide 196. The bushing 210 may be generally cylindrical and have a shape generally conforming to and providing rotating clearance for the second drill 200.

When installing the second drill guide 196 into the scapula 40, the second drill guide 196 is advanced in the direction of arrow 212. The second peg alignment pin 208 is aligned with the second peg hole 146 and the second drill guide 196 is advanced in the direction of 212 until the mounting surface 206 of the base 202 of the drill guide 196 is seated securely prepared surface 122 of the scapula 40. After the drill guide 196 is properly seated against the scapula 40, the second drill 200 is advanced downwardly in the direction of arrow 212 until the second drill 202 is fully seated in the scapula 40 and the second peg hole 198 is properly prepared.

The second drill guide 196 may optionally include a feature for controlling the depth of the second drill 202 and the corresponding depth of the second peg hole 198. For example and as is shown in FIG. 18, the depth control feature may be in the form of the stop 214 positioned on the second drill 202. The second drill 202 may be advanced downwardly in the direction of arrow 212 until the stop 214 sits against the base of the second drill guide 196. After the second peg hole 198 is fully prepared, the second drill guide may be removed from the scapula 40.

Figure 19:
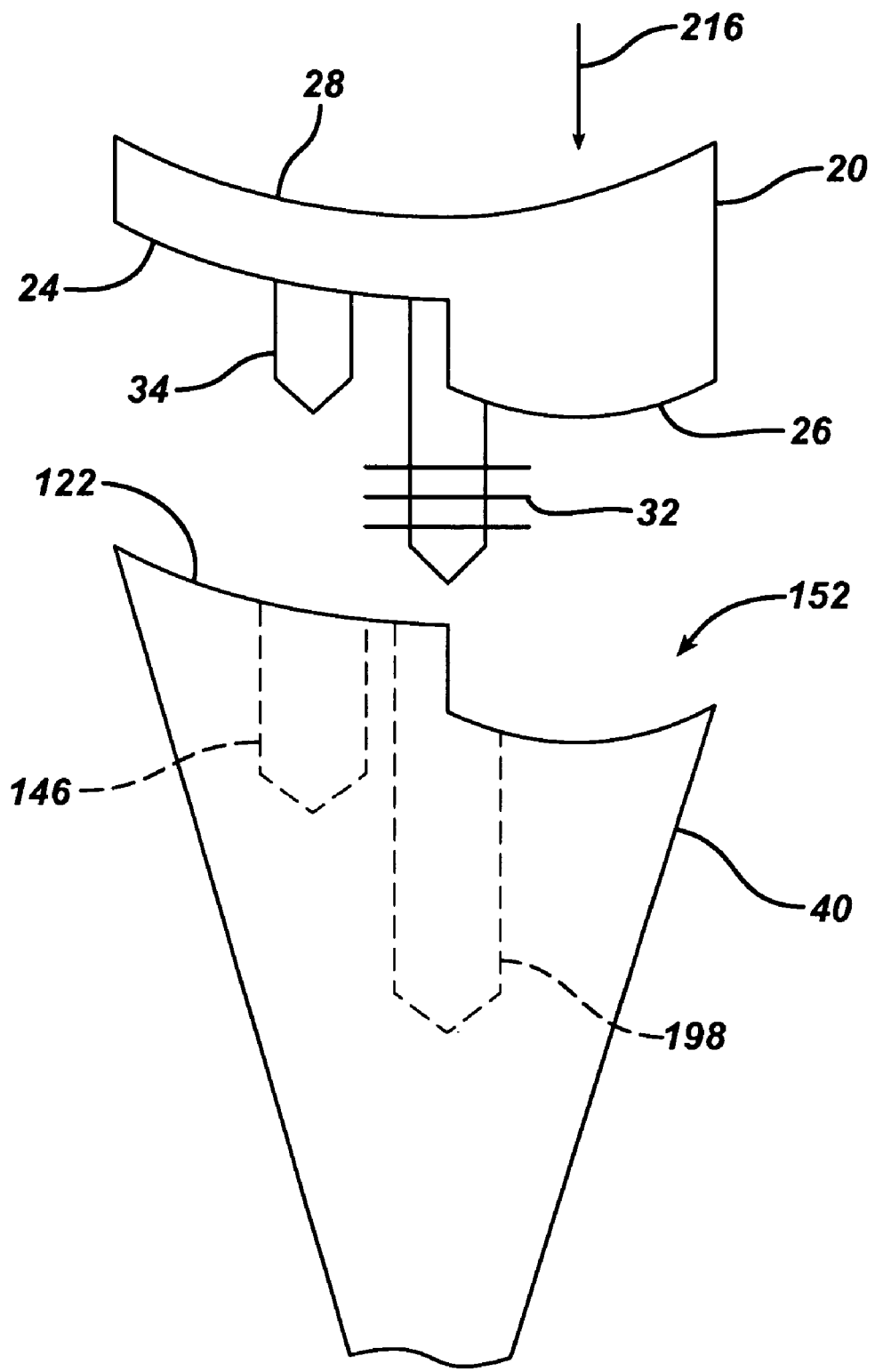
FIG. 19 is an exploded side view partially in cross section of the glenoid fossa with posterior erosion showing the mounting pocket prepared using the cutting guide of FIG. 16 and two peg holes prepared using the drill guides of FIGS. 15 and 17 and showing a glenoid component in position above the prepared surface according to an embodiment of the present invention.

Referring now to FIG. 19, the glenoid component 20 is shown in position above the mounting pocket 152 prepared by the instrument set 101 of the present invention. As can readily be seen in FIG. 19, the prepared surface 122 of the mounting pocket 152, as well as, the first peg hole 146 and the second peg hole 198 formed in the scapula 40 are adapted to provide for a proper seat of the glenoid component 20. For example, the first prepared surface 122 closely conforms to the first mounting surface 24 of the glenoid component 20. The mounting pocket 152 closely confirms to the mounting surface 26 of the glenoid component 20. Further, the first peg hole 146 in the scapula 40 closely conforms in size and position to the first peg 34 of the glenoid component 20. Similarly, the second peg hole 198 has a size, shape, and position to matingly receive the central peg 32 of the glenoid component 20.

To assemble the glenoid component 20 onto the scapula 40, the glenoid component 20 is advanced downwardly in the direction of arrow 216 until the pegs 32 and 34 align with the first peg hole 146 and the second peg hole 198, respectively. The glenoid component 20 is then further advanced in the direction of arrow 216 until the mounting surface 24 seats against the prepared surface 122 of the scapula and until the mounting surface 26 seats against the mounting pocket 152 of the scapula 40.

It should be appreciated that the instrument 100 as described in FIGS. 13-18 include only two holes being formed in the scapula 40 and appreciated that the glenoid component 20 of FIGS. 4-8 include four first pegs 34. It should be appreciated that the glenoid component 20 may include only one first peg 34 as shown in FIG. 19 or alternatively the first drill guide or the second drill guide 196 of FIG. 18, may be include additional bushing for receiving a drill for preparing the holes for receiving the additional pegs for the glenoid component 20.

Figure 20:
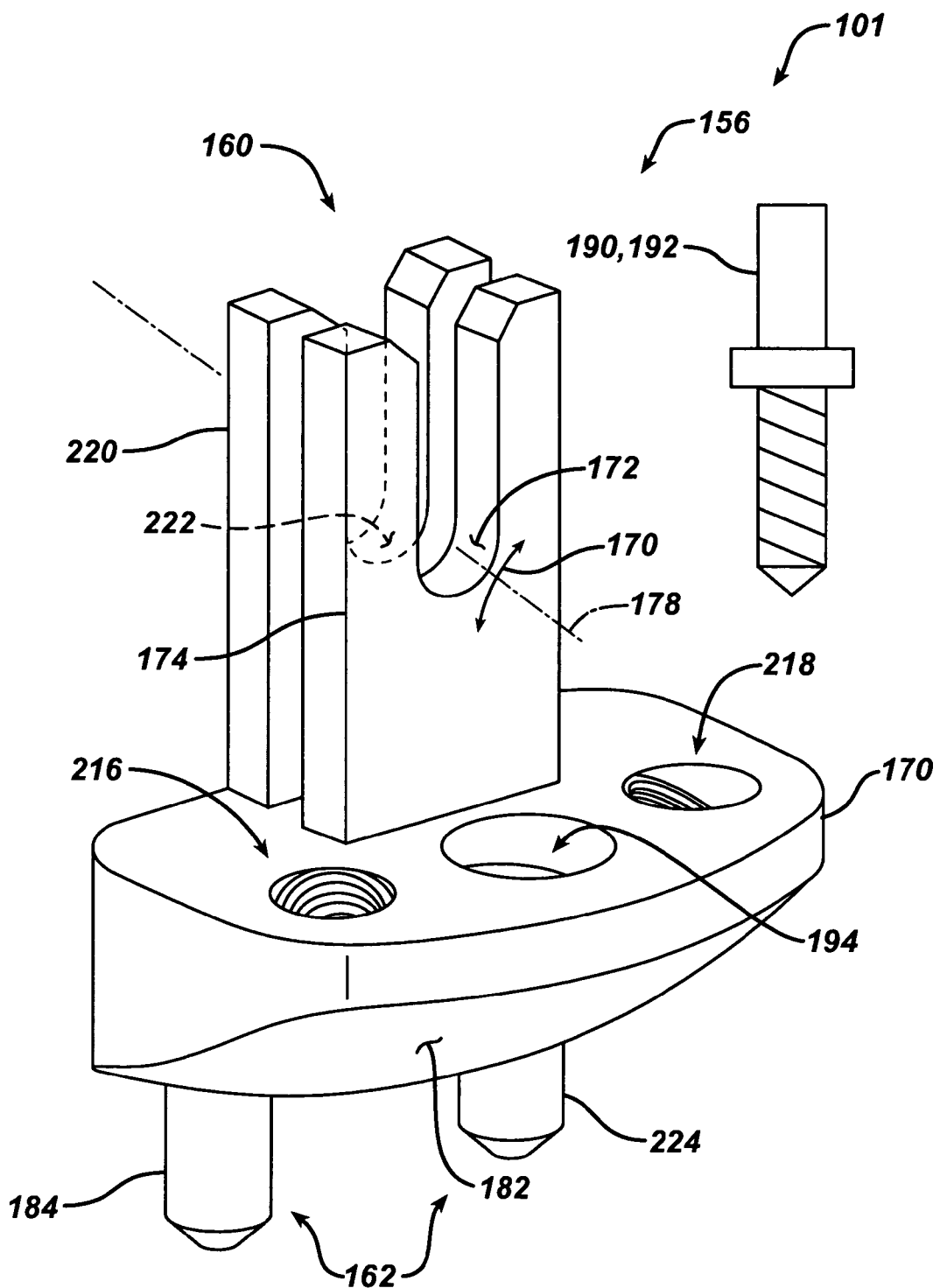
FIG. 20 is a perspective view of the base of the cutting guide of FIG. 16 according to an embodiment of the present invention.
Figure 21:
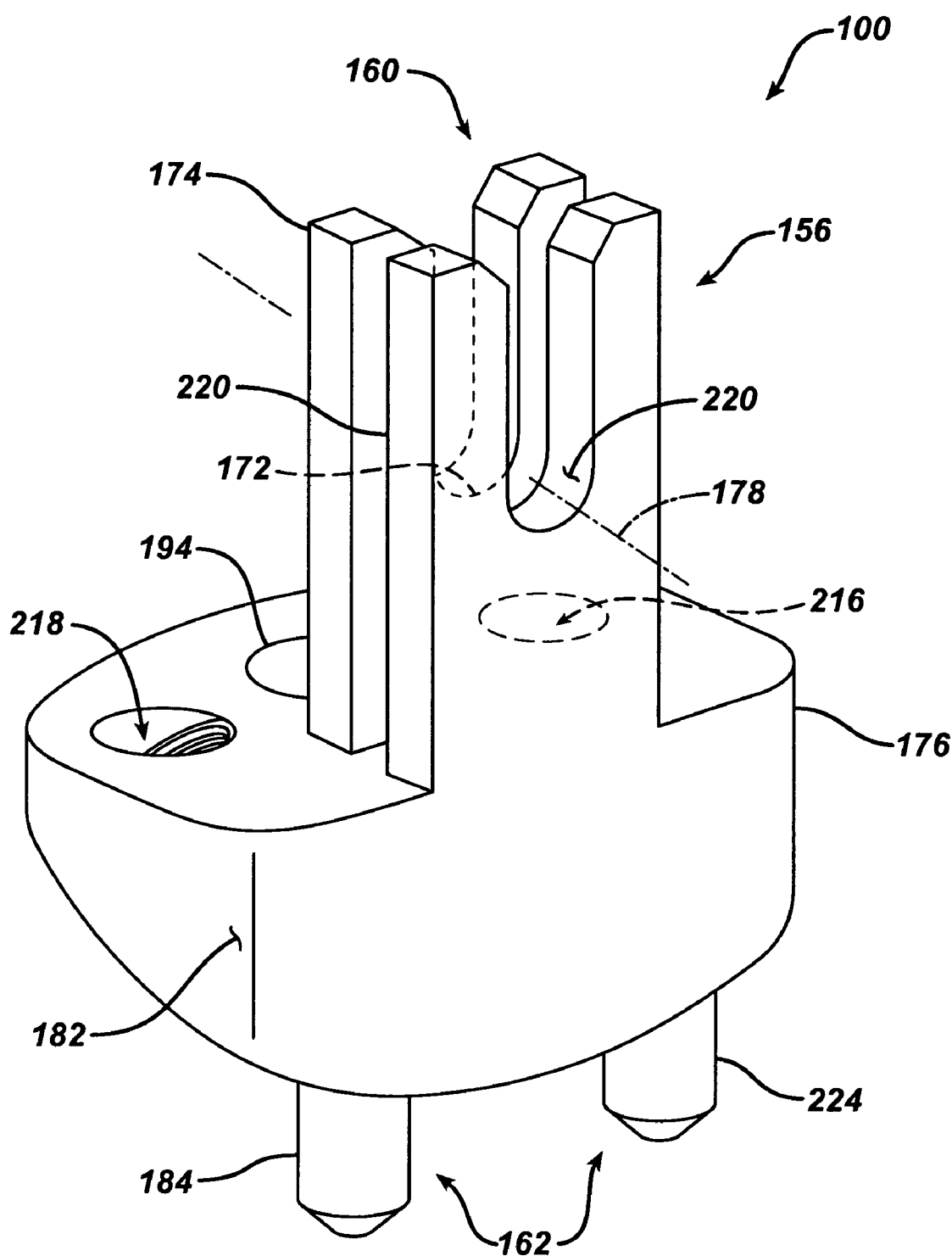
FIG. 21 is another perspective view of the base of FIG. 20.
Figure 22:
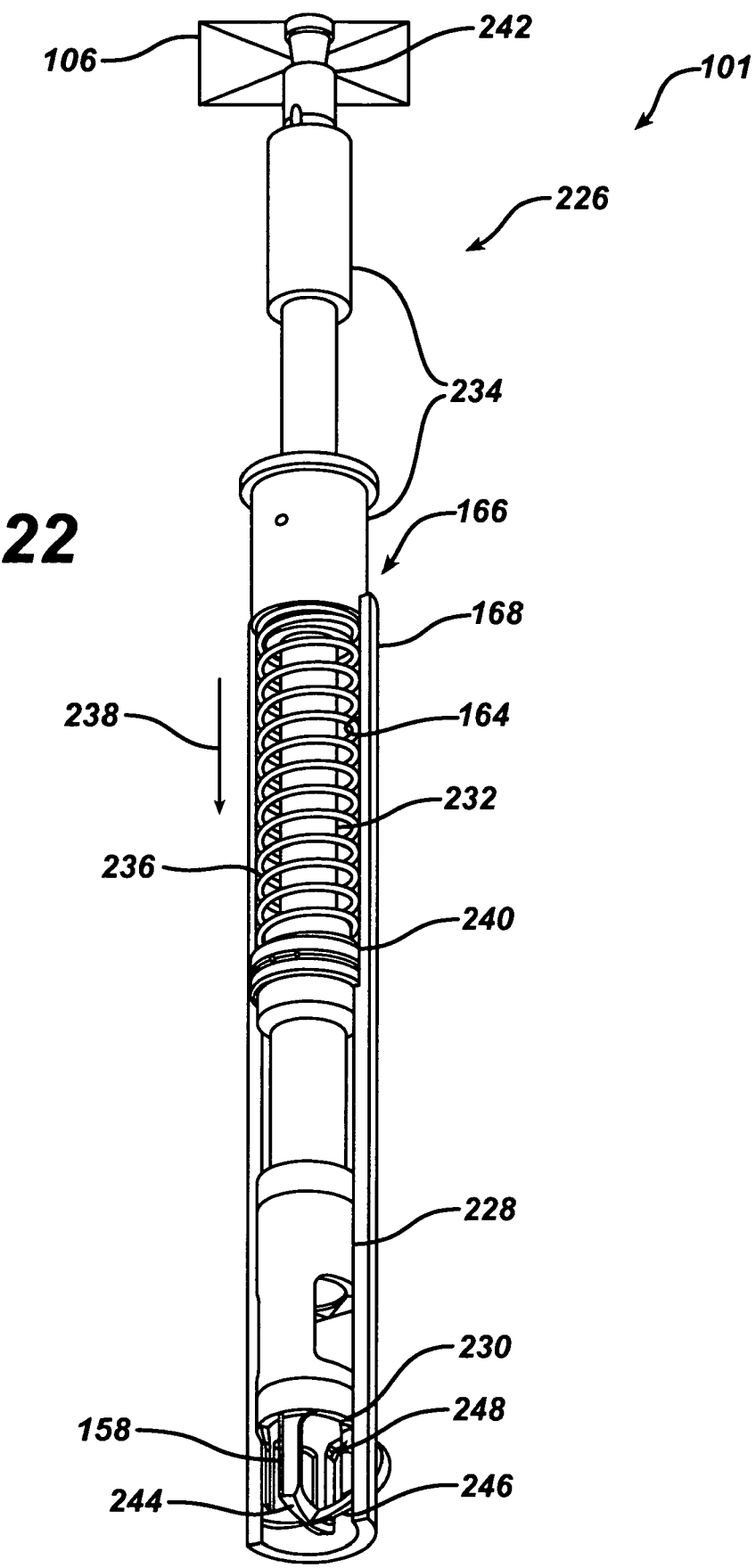
FIG. 22 is a perspective view of a cutting tool for use in preparing the mounting pocket for the posterior augmented glenoid component of FIG. 19 and a cut-away partial perspective view of the restraining component of the cutting guide for use with the base of FIG. 20 to form the cutting guide of FIG. 16 according to an embodiment of the present invention.
Figure 23:
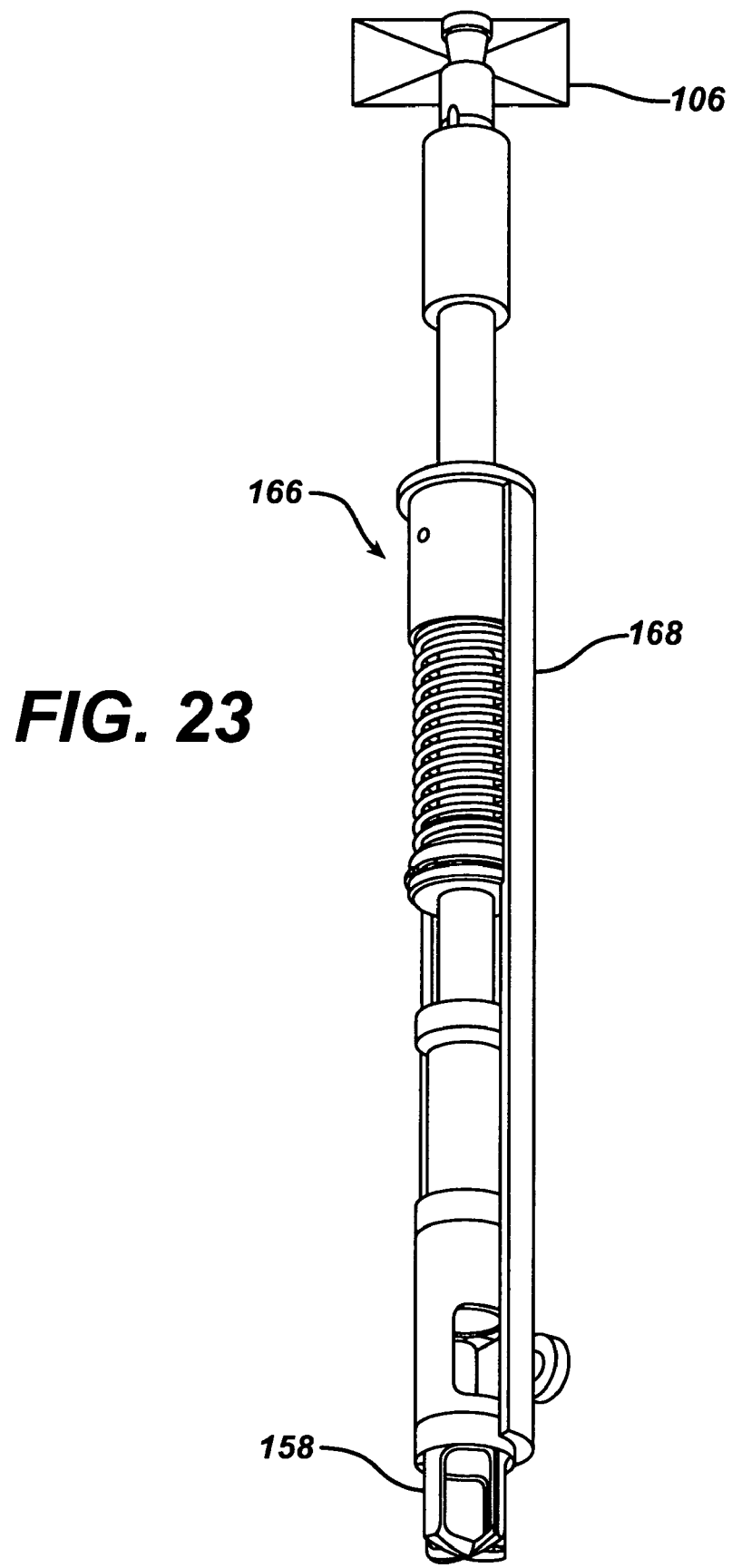
FIG. 23 is another perspective view of the cutting tool and restraining component of FIG. 22 according to an embodiment of the present invention.

Referring now to FIGS. 20 and 21, the cutting guide 156 of the instrument set 101 is shown in greater detail. The cutting guide 156 includes a base 176, which defines mounting hole 194 for passing the mounting screw 190 therethrough. Base 176 may further include a first threaded opening 216 for use with the right shoulder and a second threaded opening 218 with use with a left shoulder. The use of the two threaded holes 216 and 218 permits the cutting guide 156 to be symmetrical and therefore to be useable for both the right shoulder and the left shoulder. Base 176 further includes the mounting surface 182 which, as is shown in FIGS. 20-21, may be convex.

The cutting guide 156 further includes the guiding feature 160 as well as the locating feature 162. The guiding feature 160 may include the first post 174 in which the bearing or trunnion 172 is formed. As shown in FIGS. 20 and 21, the guiding feature 162 may include a second post 220 extending spaced from and parallel to the first post 174. The second post 220 includes a second post bearing 222, which is parallel and spaced from the first bearing 172. It should be appreciated that a solitary post 174 may be sufficient if the post 174 has a bearing of sufficient width to adequately support the cutter 158 (see FIG. 16).

The locating feature 162 may be in the form of, as shown in FIGS. 20 and 21, the mounting surface 182, as well as, the additional features in the form of, for example, the first peg hole alignment 184. It should be appreciated that the locating feature 162 may further include a second peg hole alignment pin 224 spaced from the first peg hole alignment pin 184. Pin 224 also extends from the mounting surface 182.

Referring now to FIGS. 22-25, cutting tool assembly 226 of the instrument set 101 is shown. The cutting tool assembly 226 includes sheath or housing 168. The sheath 168 is generally cylindrical and hollow. A milling cutter body 228 is rotatively fitted within the sheath 168. The milling cutter 158 extends from distal end 230 of the body 228. The body 228 is slideably positioned along the shaft portion 232 of stem 234. The body 228 is at least partially hollow for receiving the shaft portion 232 of the stem 234. A spring 236 may be utilize to urge sheath 168 distally in the direction of arrow 238 to protect the milling cutter 158. The spring 236 cooperates with shoulder 240 to urge the sheath 168 in the direction of arrow 238. A connector 242 is positioned proximally on the stem 234 for cooperation with a tool, for example, a drill 106 to drive or rotate the milling cutter 158.

The milling cutter 158 may have any suitable shape and may, as shown in FIGS. 22-25, include a plurality of flutes 244, which include cutting edges 246. Any number of plurality of flutes 244 may be utilized. For example and is shown in FIGS. 22-25, four equally spaced apart flutes 244 may be utilized. As shown in FIGS. 22-25, the milling cutter 158 may include internal openings 248 to provide a collection point for the machined bone.

Figure 24:
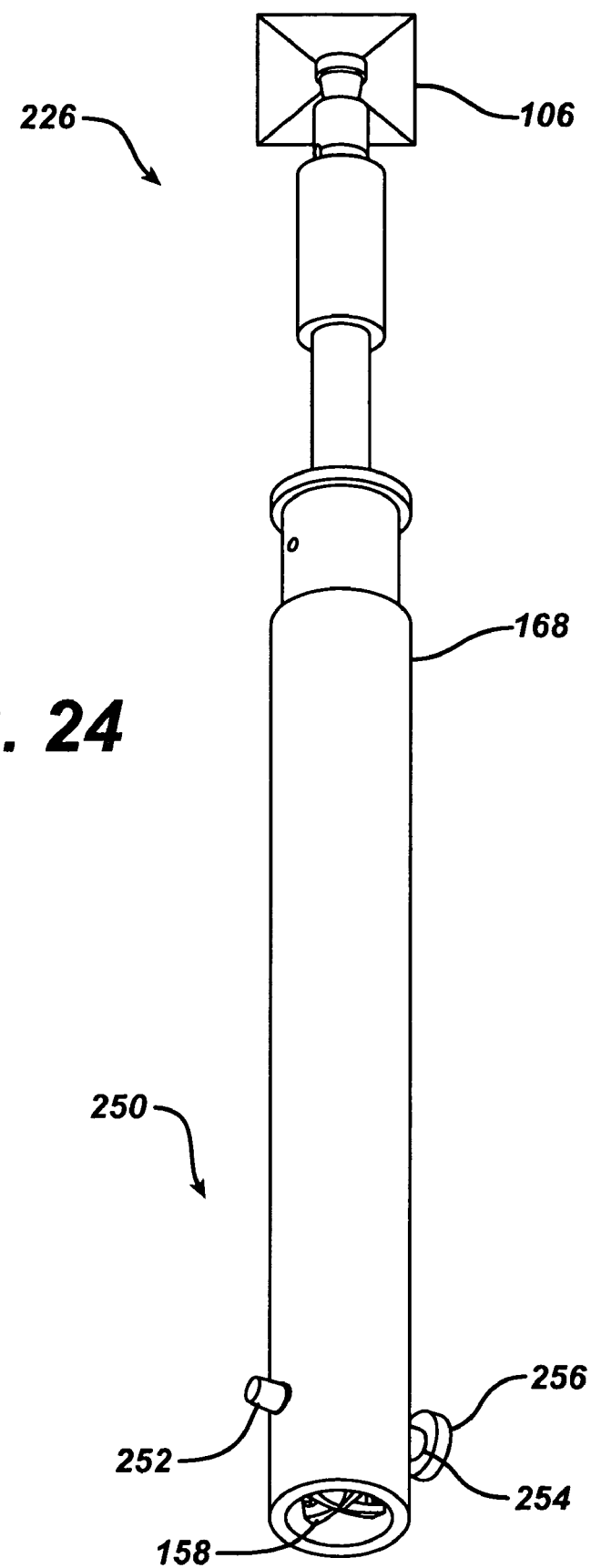
FIG. 24 is yet another perspective view of the cutting tool and restraining component of FIG. 22 according to an embodiment of the present invention showing the cutting tool in the retracted position.
Figure 25:
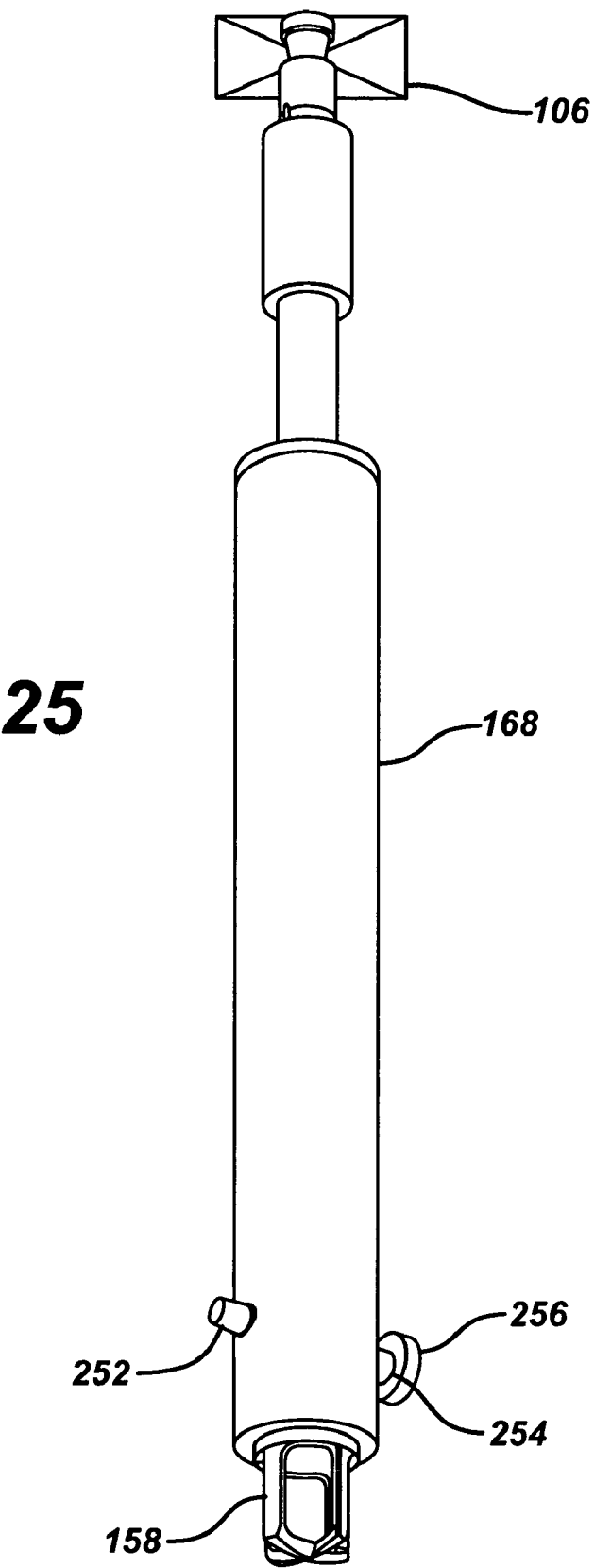
FIG. 25 is still another perspective view of the cutting tool and restraining component of FIG. 22 according to an embodiment of the present invention showing the cutting tool in the extended position.

Referring now to FIGS. 24 and 25, the cutting tool assembly 226 may be secured to the bearing 172 of the cutting guide 156 (see FIG. 16) in any suitable manner. For example and as is shown in FIGS. 24 and 25, the cutting tool assembly 226 is supported by pivoting support 250. The pivoting support 250 may have any suitable size and shape and may as shown in FIGS. 24 and 25 include a first pintle 252 extending from the sheath 168 adjacent to cutter 158. The support 250 may also include and a second pintle 254 opposed to the first pintle 252, and also extending from the cylinder 168. The first pintle 252 or the second pintle 254 or both may include a stop ring to assist in the support of the cutting tool assembly 226. As shown in FIGS. 24 and 25 the cutting tool assembly includes a stop ring 256 extending from pintle 254. At least one of the pintles, 252 or 254 may be utilized to cooperate with the bearings 172 to permit the pivoting of the cutting tool assembly 222 about axis 178 as shown in FIG. 16.

Figure 26:
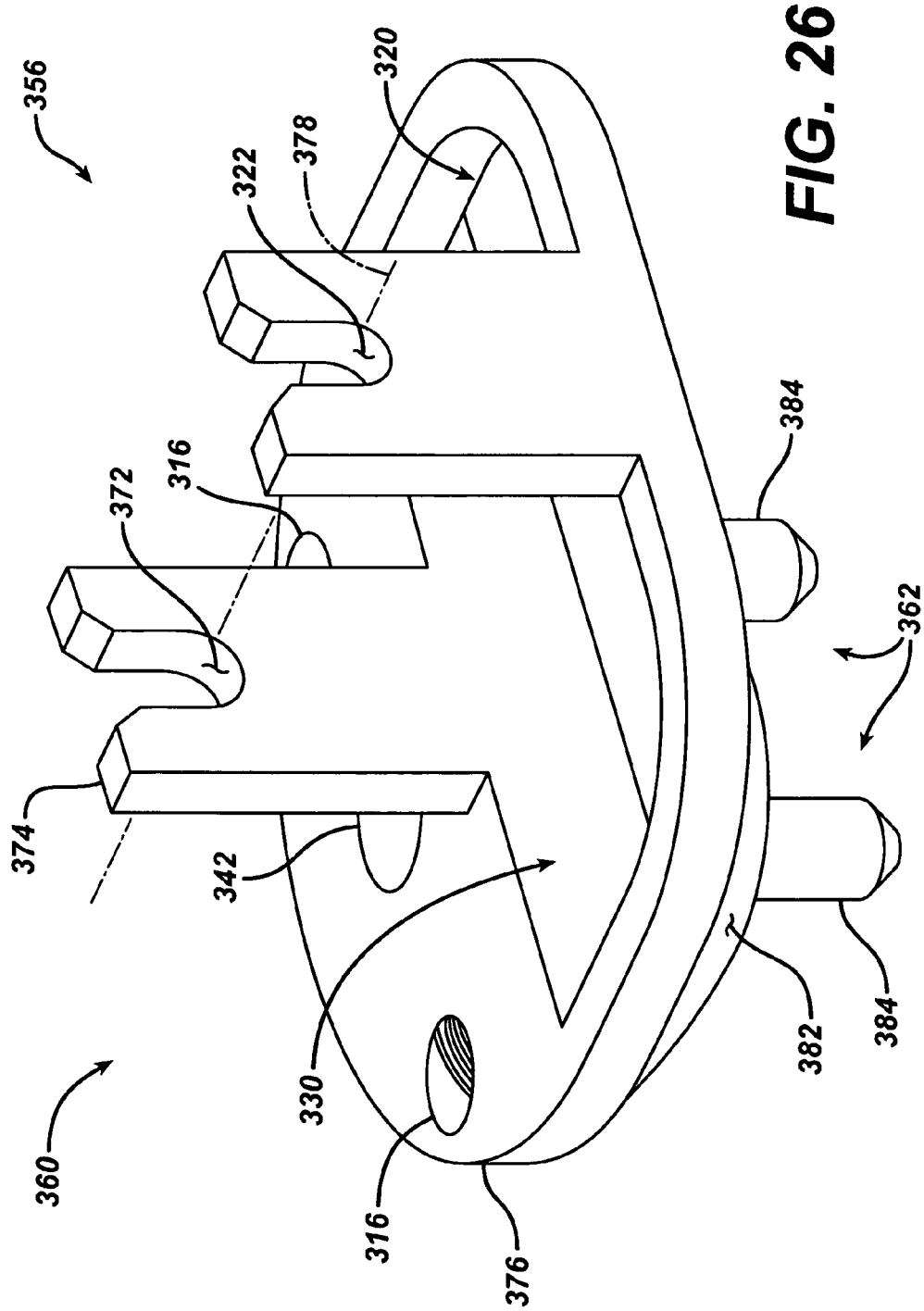
FIG. 26 is a perspective view of another embodiment of a base for the cutting guide of FIG. 16 with an outboard support.

Referring now to FIG. 26, an alternative embodiment of the cutting guide of the present invention is shown as cutting guide 356. Cutting guide 356 is similar to the cutting guide 156 of FIGS. 20 and 21. The cutting guide 356 includes a base 376. The base 376 defines convex mounting surface 382. The cutting guide 356 includes a locating feature 362 including, for example, mounting surface 382 as well as pegs 384 extending from the mounting surface 382.

The cutting guide 356 further includes a guiding feature 360 in the form of, for example, first support or post 374 and second or outward support 320. The supports 374 and 320 are utilized to define inboard bearing 372 and outboard bearing 322. The bearings 372 and 320 define longitudinal axis 378 about which the tool assembly rotates.

Unlike the cutting guide 156 of FIGS. 20 and 21, the cutting guide 356 includes both outboard and inboard bearings 372 and outboard bearing 322 that are spaced further from each other than the bearings 222 and 172 of the cutting guide 156. The bearings 372 and 322 of the cutting guide 356, unlike the bearings of the cutting guide 156, are spaced apart so that the sheath 168 of the cutting tool assembly 156 may be positioned between the inward post 274 and the outboard post 320. Since the cutting tool assembly 226 is positioned between the post 274 and the post 320, the base 276 includes a central opening or aperture 330 throughwhich the sheath 168 may rotate and through which the cutter 158 may pass.

Similar to the cutting guide 156, the cutting guide 356 of FIG. 26 includes a mounting hole 342 as well as a pair of spaced apart handle holes 316 for use with the left or right hand shoulder.

Figure 27:
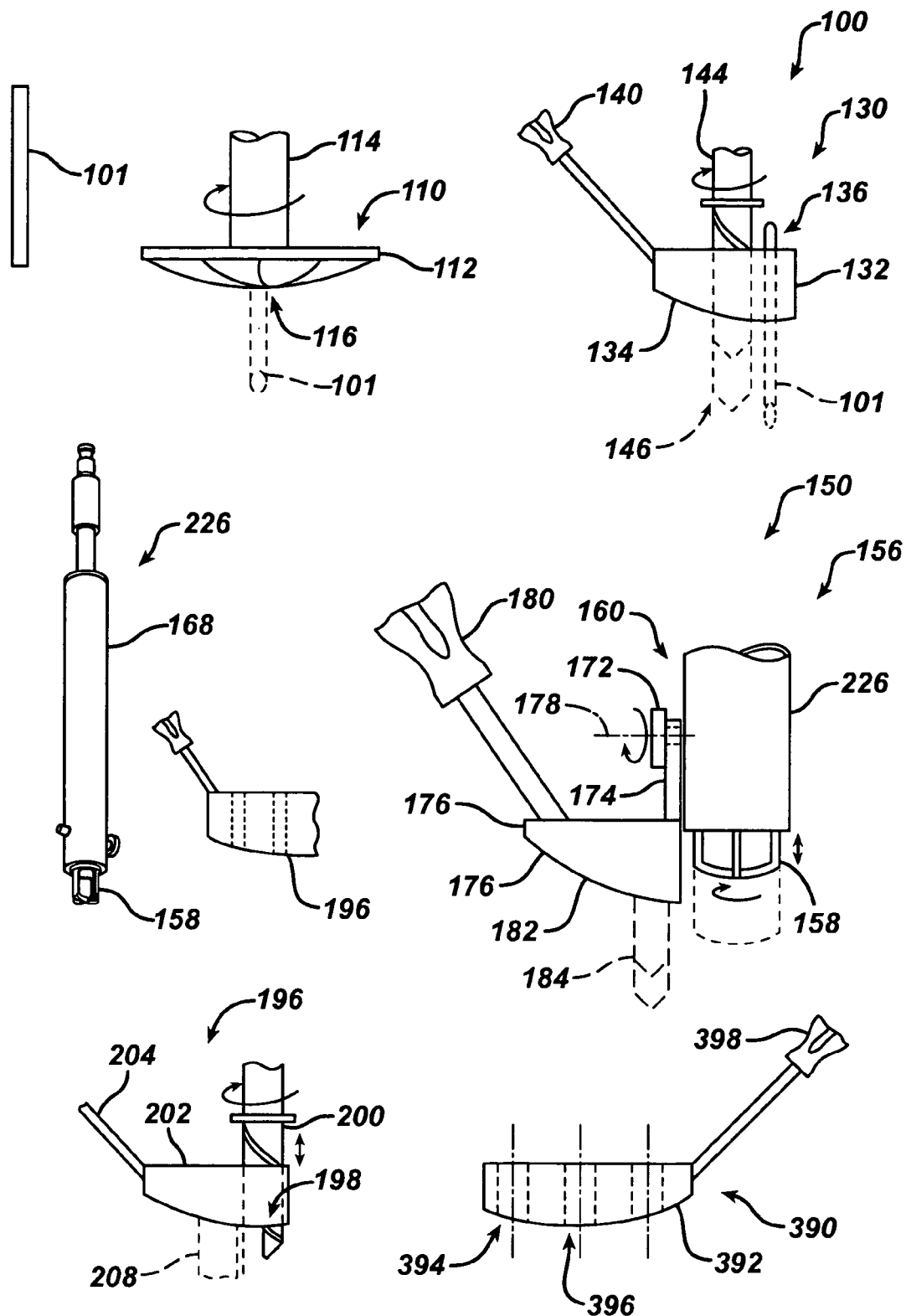
FIG. 27 is a plan view partially in cross section of a kit for use in performing shoulder arthroplasty in accordance with another embodiment of the present invention.

Referring now to FIG. 27, the instrument kit 100 is shown. The kit 100 includes a first portion tool or end mill 110 as well as a exterior pocket preparing instrument 150. The first portion tool or mill 110 may include a stem or shank 114 to which cutter 112 extends. A central opening 116 may extend through the cutter 112 and the stem 114.

The exterior pocket preparing instrument 150 may include a cutting guide 156 as well as cutting tool assembly 226. The cutting tool assembly 226 may include a sheath 168 within, which rotatable tool 158 rotates.

The cutting guide 156 may include a base 176, which defines locating surface 182. Cutting guide 156 includes a first feature or guiding feature 160, which include a bearing 172 for supporting the cutting tool assembly 226. The bearing 172 is supported by a post 174 extending from the base 176. The cutting guide 176 further includes a second feature or positioning feature 162. The positioning feature 162 may include the locating surface 182 as well as, for example, protrusions in the form of, for example, pin 184. A handle 180 may be utilized to guide the cutting guide 156 into position unto the glenoid.

Additional items may be a part of the instrument set on kit 100. For example, the instrument set 101 may include a pin 100 for use with positioning the end mill 110. The instrument 110 may further include a drill guide 130 for preparing a first peg opening 146. The first drill guide 130 may include a base 132, which defines an opening 136 for receiving the alignment pin 100 as well as a support surface 134. A drill 144 may be utilized with the first drill guide 130 and pass there through. A handle 140 may be utilize to properly position the first drill guide 130.

The instrument kit 101 may further include an additional drill guide 196. The drill guide 196 may be utilized for preparing the second peg hole 198. The second drill guide 196 may include a base 202 from which second peg hole alignment pin 208 extends. The base 202 is adapted for receiving and guiding drill 200 to form second peg hole 198. Drill guide 196 may include a handle 204 for positioning the guide 196.

The instrument kit 100 may further include an additional drill guide 390 for preparing additional peg holes for the glenoid component. For example, the instrument kit 100 may include drill guide 300 having a base 392 including for example, first opening 394 and second opening 396 for receiving a drill to prepare additional peg holes. Drill guide 390 may include a handle 398 for assisting in positioning the guide 390.

Figure 28:
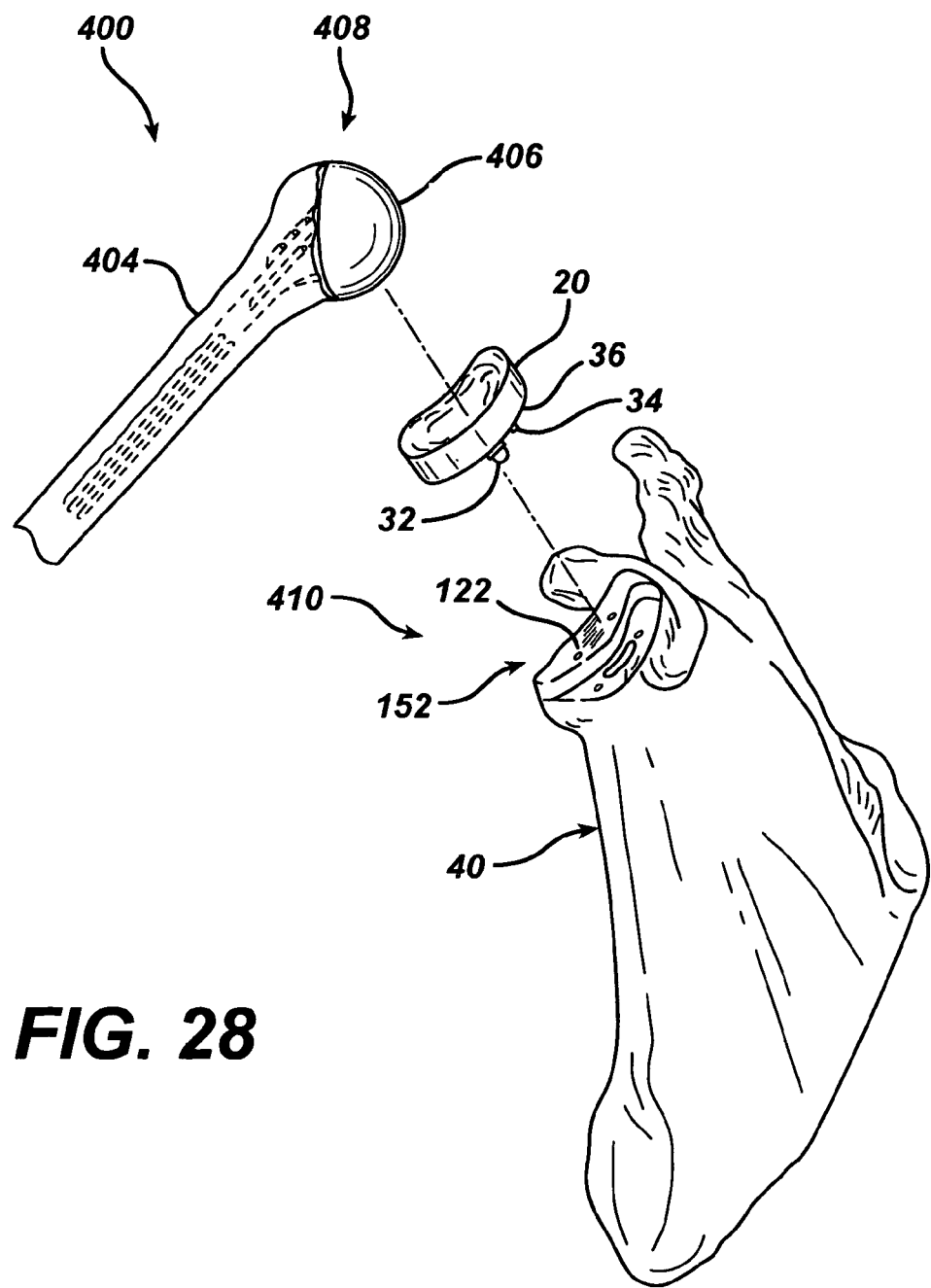
FIG. 28 is an exploded perspective view of glenoid vault of a scapula, a humerus, and an augmented glenoid for use in the cavity of a glenoid prepared with the instruments of the present invention.

Referring now to FIG. 28, humeral prosthesis 400 is shown for use with a glenoid pocket 410 prepared by the instruments of the present invention. The prosthesis assembly 400 includes a humeral prosthesis 408 positioned on humerus 404. The humeral prosthesis 408 includes a head 406 extending from the humeral stem 402. The humeral stem 402 and humeral head 406 form humeral prosthesis 408. Glenoid component 20 cooperates with head 406 of the humeral prosthesis 408. The glenoid component 20 is positioned in prepared pocket 410 including prepared surface 122 as well as mounting pocket 152 formed on scapula 40 with the instruments of the present inventions.

Figure 29:
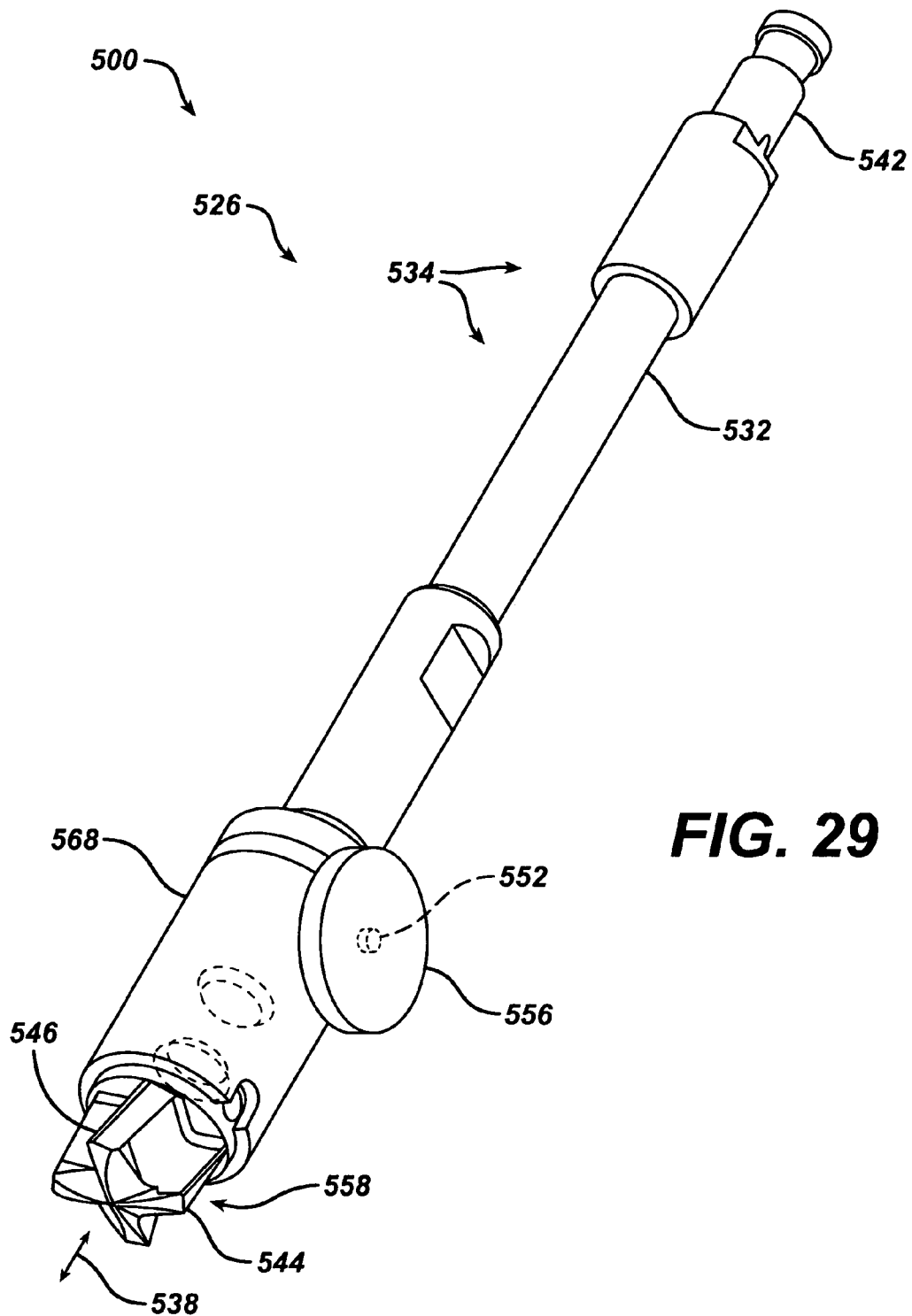
FIG. 29 is a perspective view of a cutting tool assembly according to another embodiment of the present invention.
Figure 30:
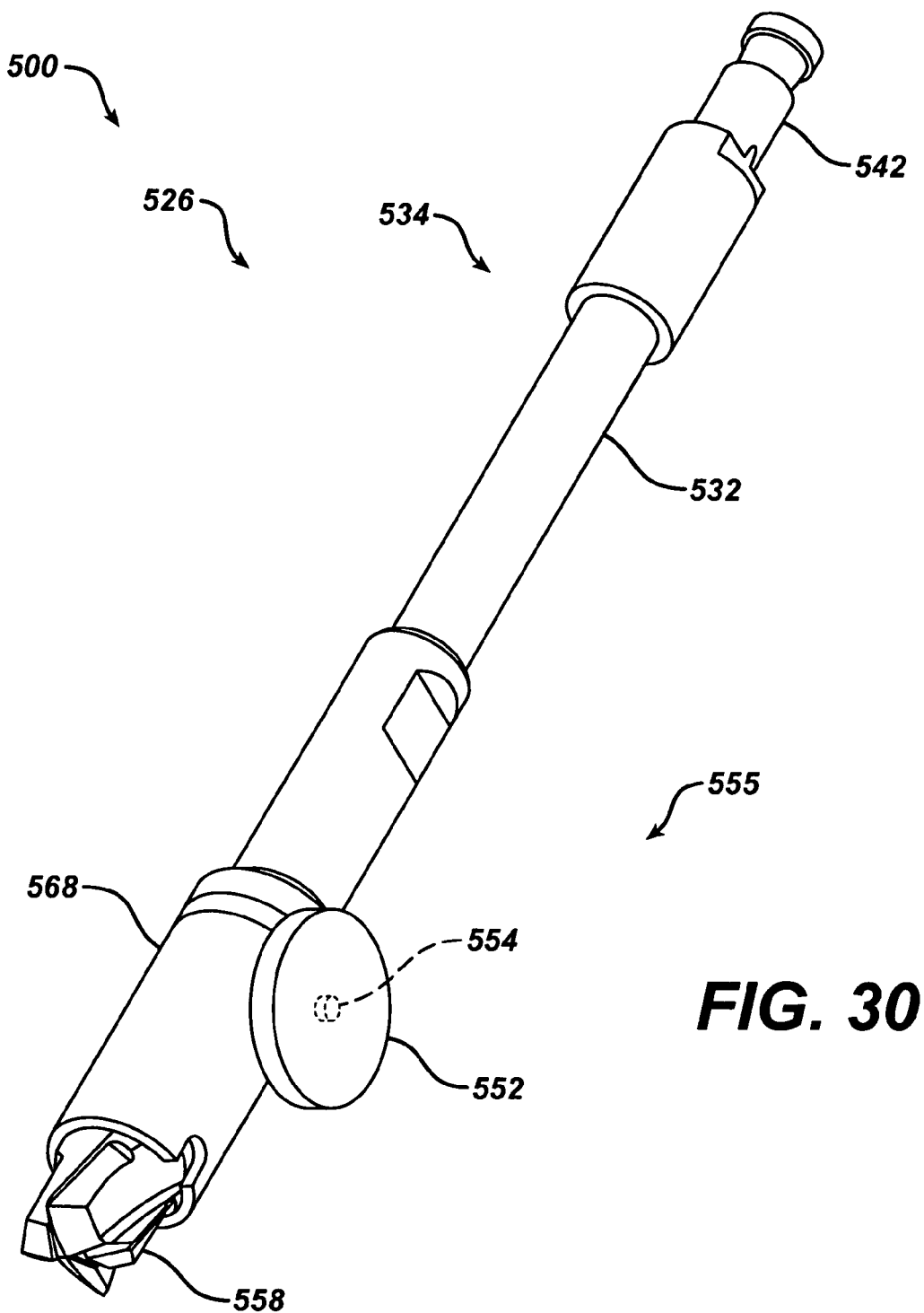
FIG. 30 is a perspective view of the cutting total assembly of FIG. 29.
Figure 31:
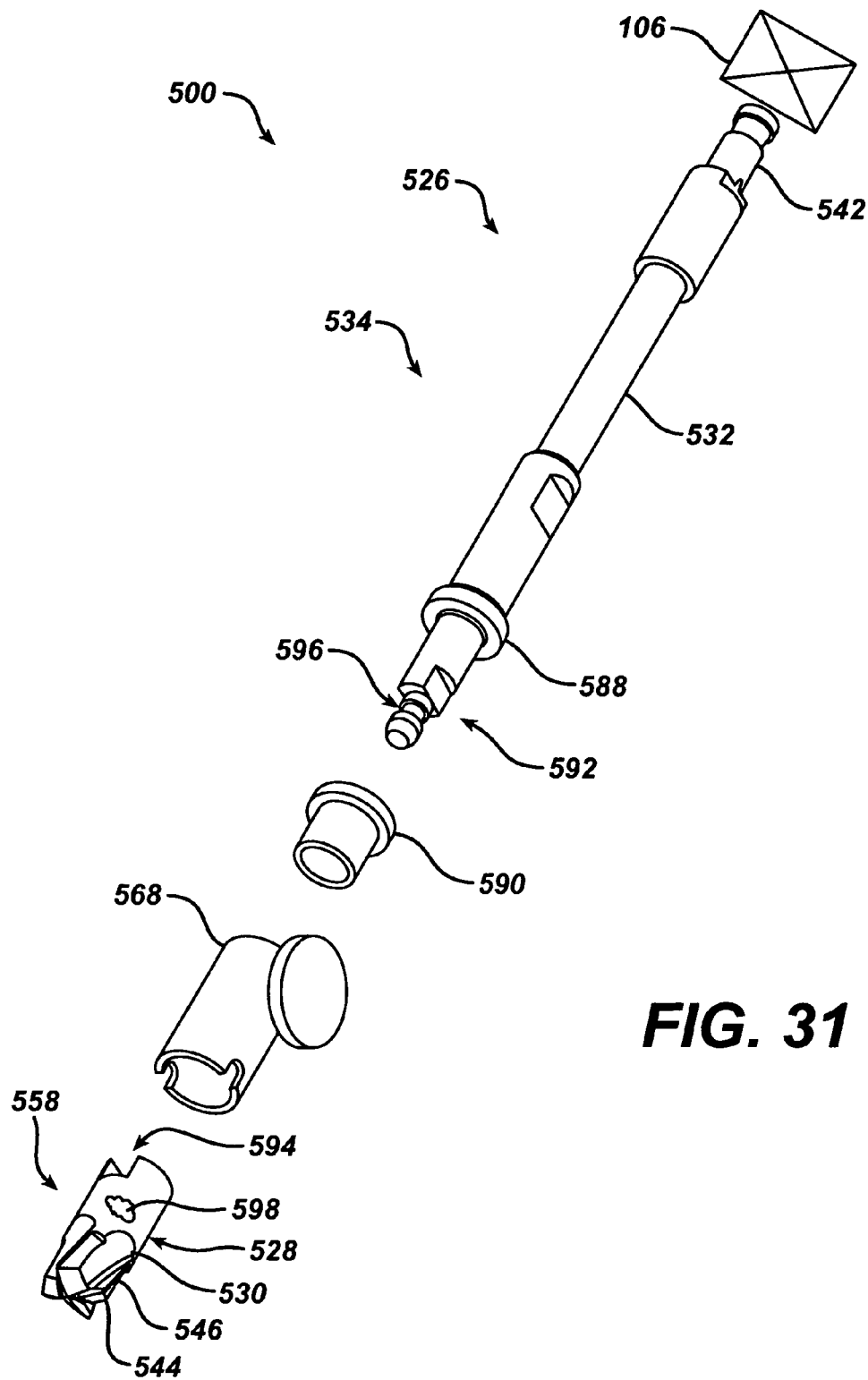
FIG. 31 is an exploded perspective view of the cutting tool assembly of FIG. 29.

Referring now to FIGS. 29, 30, and 31, another embodiment of the present invention is shown as cutting tool assembly 526 of an instrument set 500 is shown. The cutting tool assembly 526 includes a sheath or housing 568. The sheath 568 is generally cylindrical and hollow. A milling cutter body 558 is rotatably fixed within the sheath 168. The milling cutter 558 extends from the distal end 530 of the body 528. The body 528 is slidably engagable with stem 534. The body 528 defines a female cutter connection 594, which engages with male cutter connection 592 formed on stem 534. The male cutter connection 592 may include a groove 596, which mates with a helical spring 598 positioned in the female cutter connection 594 of the milling cutter body 528, the sheath 568, and the stem 534 may be made of a metal. If made of a metal, the metal may be a cobalt chromium alloy, a stainless alloy, or a titanium alloy. The bushing 590 may also be made of any suitable, durable material but preferably is made of a material that provide a bearing function for the cutting tool assembly. For example, the bushing 590 may be made of a plastic, for example, acetal copolymer.

The milling cutter 558 may have any suitable shape and may include a plurality of flutes 544 including the cutting edges 546. Any number of plurality of flutes 544 may be utilized. For example, and is shown in FIG. 29-31, four equally spaced apart flutes 544 may be utilized.

The cutting tool assembly 526 may include a connector 542 for connection with the driving tool, for example, a power drill 106.

The stem 534 may have any suitable shape and may include a shaft portion 532 positioned between the connector 542 and male connector 592. A collar 588 may be positioned between the shaft 532 and the male connection 592. The collar 588 serves a axial seat for the bushing 590.

Figure 32:
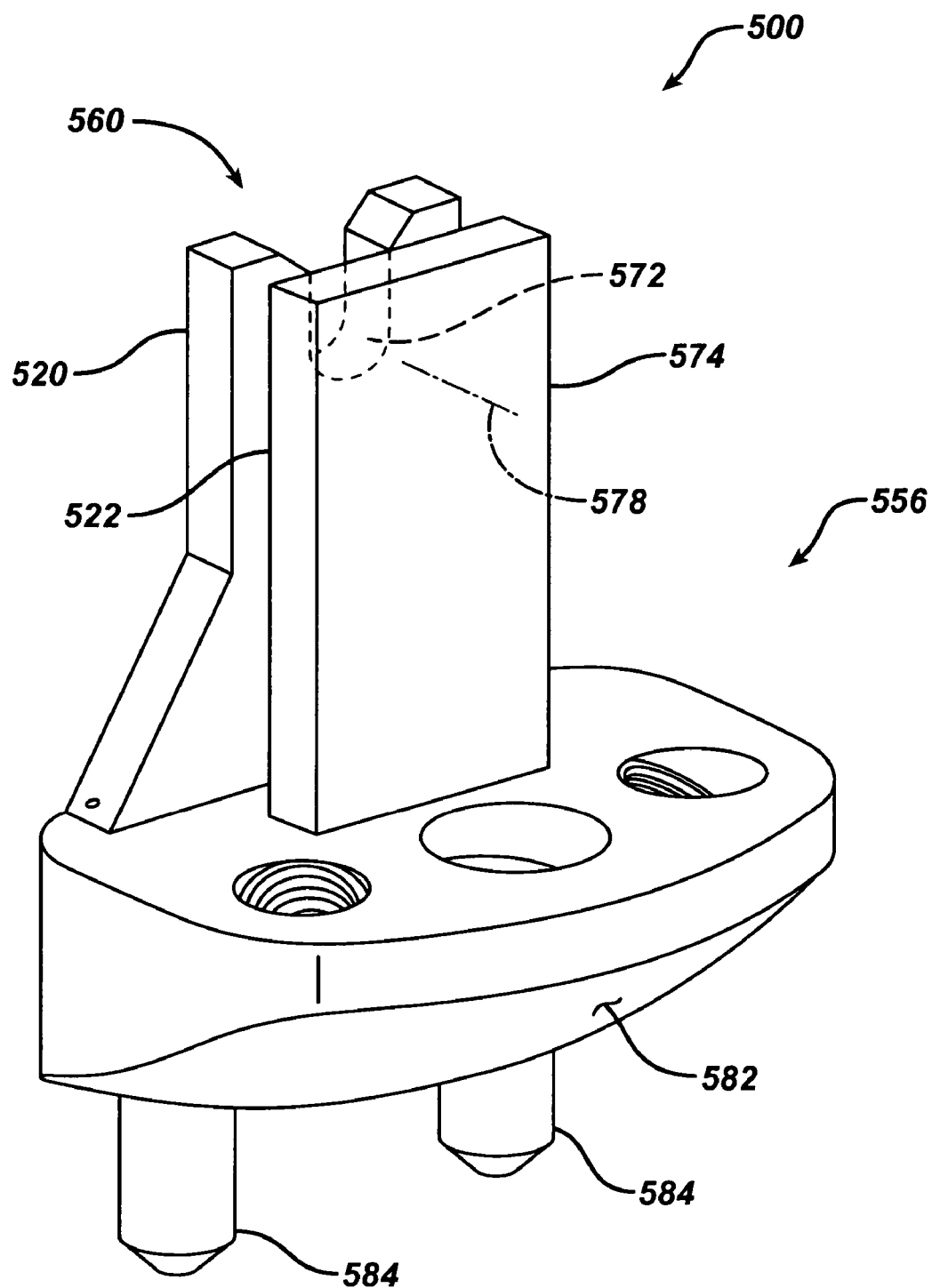
FIG. 32 is a perspective view of a cutting guide for use with the cutting assembly tool of FIG. 29 is accordance to an embodiment of the present invention.

Referring now to FIG. 32, an alternate embodiment of the cutting guide of the present invention is shown as cutting guide 556. The cutting guide 556 is similar to the cutting guide 156 of FIGS. 20-21. The cutting guide 556 is designed for use with the cutting tool assembly 526 of FIG. 29-31. The cutting guide 556 includes a base 576. The base 576 defines convex mounting surface 582. The cutting guide 556 includes a locating feature 562 including, for example, mounting surface 582 as well as pegs 584 extending from the mounting surface 582.

The cutting guide 556 further includes a guiding feature 560 in the form of, for example, a first support or post 574 and a second post or bearing 520. The support 574 and 520 are utilized to define bearing 572 and stop 522. The bearing 520 defines longitudinal axis 578 about which the tool assembly rotates.

Referring again to FIG. 30, cutting assembly mounting mechanism 555 is shown. The cutting assembly mounting mechanism 555 cooperates with the guiding feature 560 of the cutting guide 556 of FIG. 32. The cutter assembly mounting mechanism 555, as shown in FIG. 30, includes a stop ring 552 extending outwardly from pintle 554. The pintle 554 is designed to rotate on bearing on trunnion 572 of guiding feature 560 of the cutting guide 556 of FIG. 32. The stop ring 552 is positioned between stop 522 of the first post 574 and the second post 520.

The milling cutting body 528, the sheath 568, and the stem 534 may be made by an suitable, durable material. For example, the milling cutter body 528, sheath 568 and stem 534 may be made of a metal, for example, a cobalt chromium alloy, a stainless steel alloy, or a titanium alloy.

Figure 33:
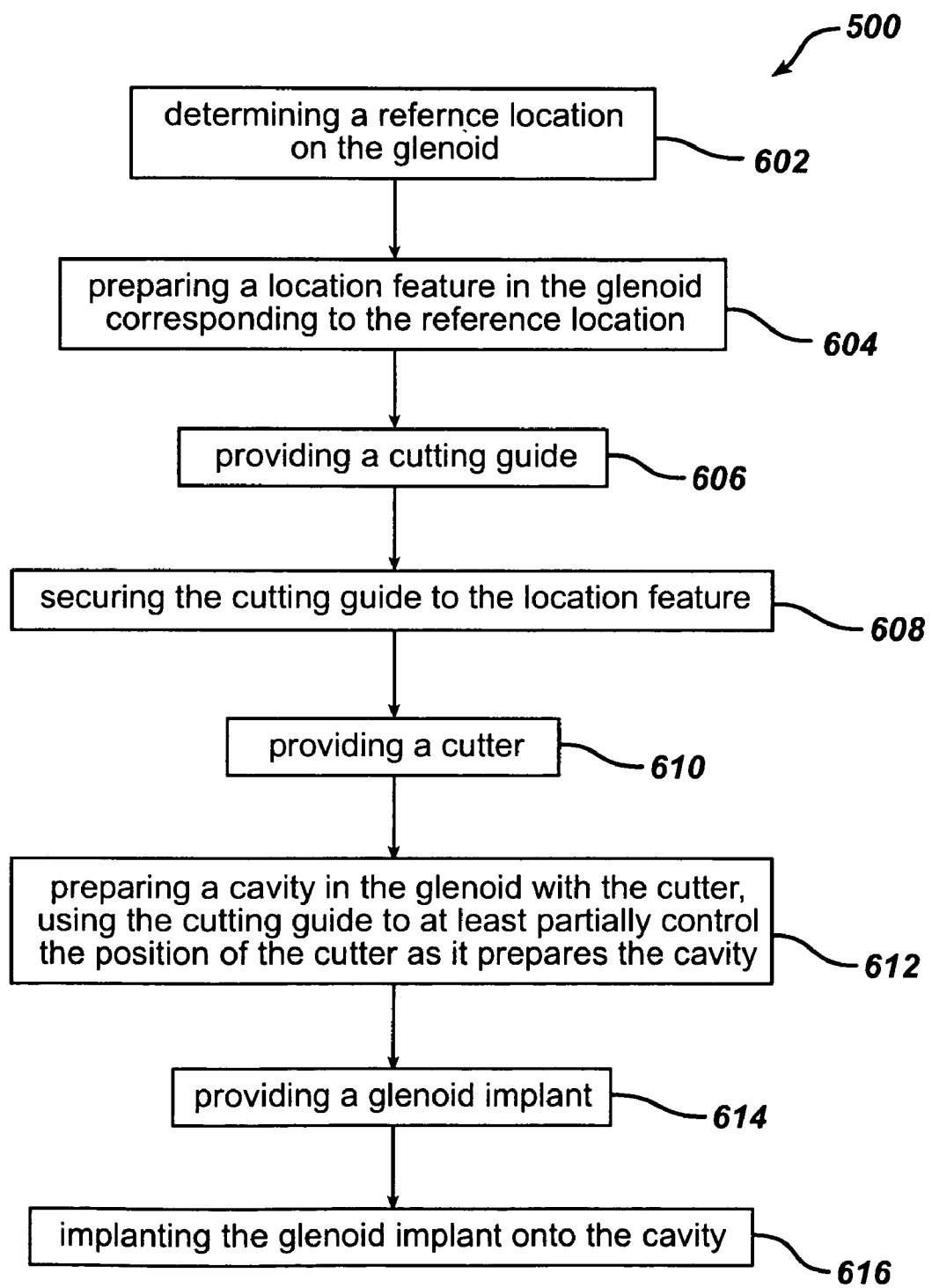
FIG. 33 is a flow chart of a method for performing shoulder arthroplasty in accordance with yet another embodiment of the present invention.

Referring now to FIG. 33, a method of performing shoulder arthoplasty is method 600. The method 600 includes first step 602 of determining a preference location on the glenoid and a second step 604 and preparing a location feature in the glenoid corresponding to reference location.

The method 600 further includes a seventh step 614 of providing a glenoid implant and an eighth step 616 of implanting the glenoid implant into the cavity.

The method 600 further includes a third step 606 of providing a cutting guide and a fourth step 608 of securing the cutting to the location feature. The method 600 further includes a fifth step 610 of providing a cutter and a sixth step 612 of preparing a cavity with the glenoid cutter and using the cutter guide to at least partially control the position of the cutter as prepares the cavity.

Figure 34:
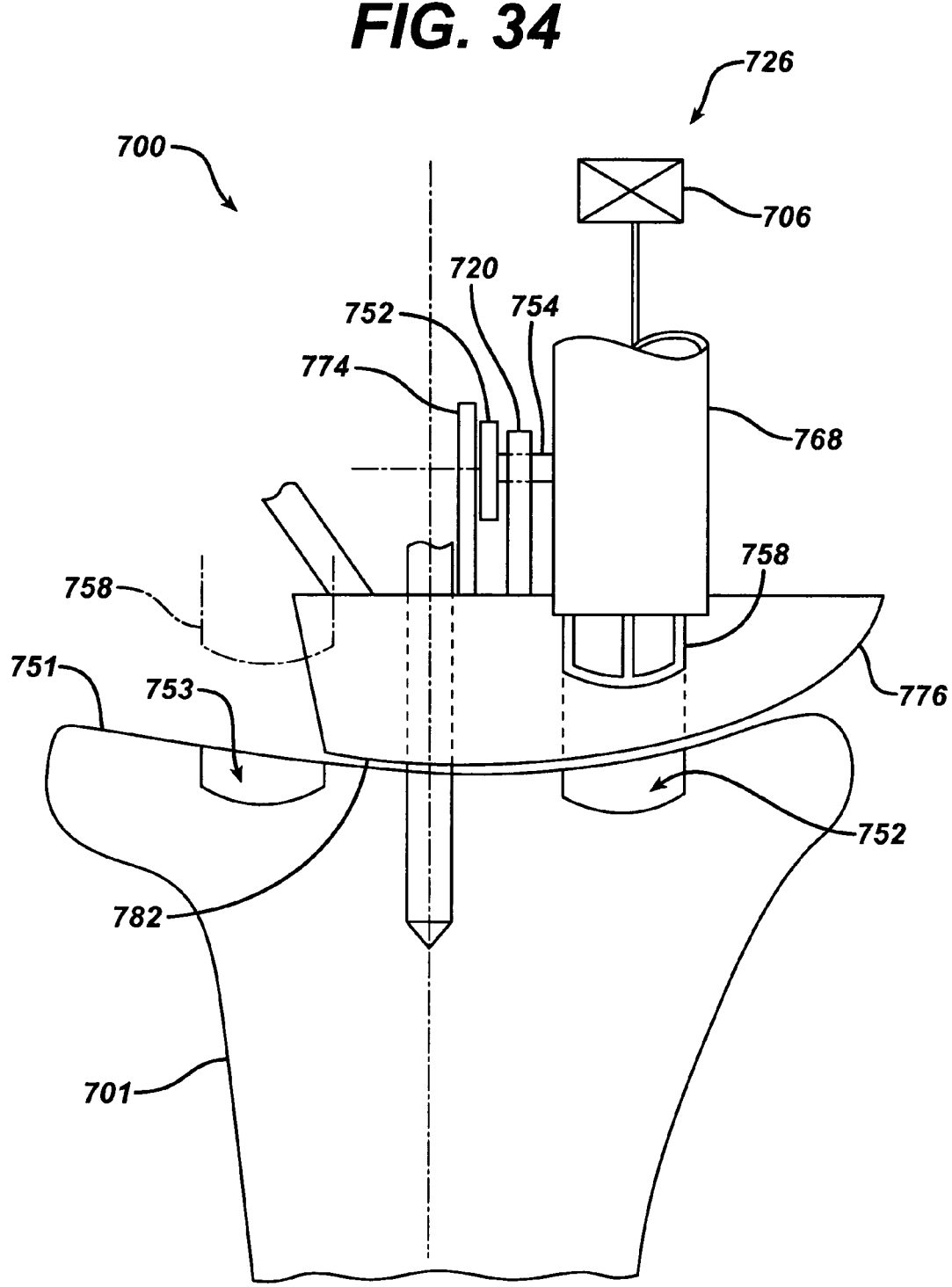
FIG. 34 is plan view of a cutting tool assembly for use on a tibia for preparing a tibia for a knee prosthesis according to another embodiment of the present invention.

According to the present invention and referring now to FIG. 34, another embodiment of the present invention is shown as instrument set 700. The instrument set 700 is similar to the instrument set 101 of FIGS. 13-25 and also similar to the instrument set 500 of FIGS. 29-32. The instrument set 700 includes a cutting guide 756 similar to the cutting guide 556 of FIG. 32. The instrument 700 further includes a cutting tool assembly 726 for cooperation with the cutting guide 756. The cutting tool assembly 726 is generally similar to the cutting tool assembly 526 of FIGS. 29-31.

The instrument set 700 shown in FIG. 34, is adapted for use in preparing mounting pockets 752 and 753 on the tibia 701. The mounting pocket 752 and 753 may be used to receive a portion of a unitary tibial (not shown), tray as part of a knee prosthesis (not shown), or the mounting pocket 752 may be used to receive a medial partial tibial component (not shown) of a partial knee prosthesis (not shown). For example, the mounting pocket 753 may be adapted for receiving a lateral partial tibial component of the partial knee prosthesis.

The cutting tool assembly 726 is mountable on the cutting guide 756. The cutting guide 756 may include a base 776 including surface ???? 782 for cooperation with prepared surface 751 of the tibia 701. The prepared surface 751 may be prepared by tools similar to that of the instrument set 101 of FIGS. 13-25.

Supports in the forms of bearing 720 and post 774 may extend from the base 776.

The cutting tool assembly 726 may include a cylindrical body 768 which is hollow. A tool cutter 758 may be rotatably fitted within the cylinder 768. The tool cutter 758 may be connected to, for example, power source 706. The power source 706 may be in the form of, for example, a power drill. A pintle 754 may extend from the cylinder 768. The pintle 754 rests on trunnion 772 formed on the bearing 720. A stop ring 752 may extend outwardly from the pintle 754. The stop ring 752 is constrained between bearing 720 and post 774 of the cutting guide 756. The stop ring 754 and the pintle 754 comprise the mounting mechanism 755 of the cutting tool assembly 756. The mounting mechanism 755 of the cutting tool assembly 726 cooperates with first feature 760 of the cutting guide 756. The first feature 760 includes the bearing 720 and the post 774.

The cylinder 768 of the cutting tool assembly 726 pivots about trunnion 776 providing a path for the tool cutter 758 so that the tool cutter 758 may create mounting pockets 752.

It should be appreciated that the cutting guide 756 may be positioned in a post position on the tibia 701 opposed to that position as shown in FIG. 34. In such a second position the cutting tool 758, as shown in phantom, in positioned over the second mounting pocket 753. By doing so, the cutting tool assembly 726 and the cutting guide 756 may be used to prepare the first mounting pocket 752 as well as the second mounting pocket 753 of the tibia 701.

It should be appreciated that the instrument set of the present invention may be utilized to prepare pockets or portions of a joint within the body to prepare a surface for mounting a prosthesis. For example, the instrument set of the present invention may be utilized to prepare a surface on the femur, the humerus, the ulna, the radius, or the tibia.

Although the present invention and its advantages have been described in detail, it should be understood that various changes, substitutions, and alterations can be made therein without departing from the spirit and scope of the present invention as defined by the appended claims.

We claim:

1. An instrument assembly for preparing a surface of a joint, the surface adapted for receiving a glenoid component having a feature closely conforming to the glenoid surface, the prosthetic component providing a bearing surface for a portion of a long bone, the instrument assembly comprising:
    a guide having a housing, a base and a restraining component, said base including a convex lower surface sized and shaped to be seated in the prepared joint surface and the restraining component operably associated with said base, the restraining component being pivotably and removably coupled to the housing, the housing including a pintle and the restraining component including a bearing having a u-shaped slot, wherein the pintle slidably fits within the u-shaped slot; and
    a tool for cooperation with the housing for preparing the surface, the housing adapted to at least partially control the position of the tool as it prepares the surface, the base adapted to assist in positioning of the guide with respect to the joint.

2. An instrument assembly as in claim 1, wherein the base of said guide further comprises a pin.

3. An instrument assembly as in claim 1:
    wherein the housing of said guide is defined by a wall in said guide forming a cylindrical opening; and
    wherein said tool comprises a rotatable tool fitted to the cylindrical opening.

4. An instrument assembly as in claim 1, wherein said tool comprises a milling tool.

5. An instrument assembly as in claim 1, wherein said base further comprises a protrusion extending from the convex lower surface for cooperation with the joint.

6. An instrument assembly as in claim 1, wherein said bearing defines a bearing centerline of rotation and wherein said centerline is generally parallel to the convex surface of said base.

7. An instrument assembly as in claim 1, further comprising a handle for positioning the guide with respect to the joint.

8. An instrument assembly for preparing a feature on a scapula, the feature adapted for receiving an augmented glenoid component for providing a bearing surface for a head portion of a humerus, the instrument assembly comprising:
    a guide including a housing, a base and a restraining component, the base including a convex lower surface sized and shaped to be seated in the prepared joint surface and the restraining component operably associated with said base, the restraining component being pivotably and removably coupled to the housing, the housing including a pintle and the restraining component including a bearing having a u-shaped slot, wherein the pintle slidably fits within the u-shaped slot; and
    a tool for cooperation with the housing for preparing the glenoid surface, the housing adapted to at least partially guide the tool as it prepares the feature, the base adapted to assist in locating the guide with respect to the scapula.

9. An instrument assembly as in claim 8:
    wherein the housing of said guide is defined by a wall in said guide forming a cylindrical opening; and
    wherein said tool comprises a rotatable tool fitted to the cylindrical opening.

10. An instrument assembly as in claim 8, wherein said tool comprises a milling tool.

11. An instrument assembly as in claim 8, wherein said base further comprises a protrusion extending from the convex lower surface for cooperation with the scapula.

12. An instrument assembly as in claim 8, wherein said bearing defines a bearing centerline of rotation and wherein said centerline is generally parallel to the convex surface of said base.

13. An instrument assembly as in claim 8, further comprising a handle for positioning the guide with respect to the glenoid fossa.

* * * * *